US008936720B2

(12) United States Patent  
Childers et al.

(10) Patent No.: US 8,936,720 B2  
(45) Date of Patent: Jan. 20, 2015

(54) DRAIN AND FILL LOGIC FOR AUTOMATED PERITONEAL DIALYSIS

(75) Inventors: Robert W. Childers, Trinity, FL (US);  
Ying-Cheng Lo, Green Oaks, IL (US);  
Peter Hopping, Lutz, FL (US)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 473 days.

(21) Appl. No.: 13/195,376

(22) Filed: Aug. 1, 2011

(65) Prior Publication Data

US 2012/0071815 A1    Mar. 22, 2012

Related U.S. Application Data

(60) Provisional application No. 61/384,001, filed on Sep. 17, 2010.

(51) Int. Cl.
*A61M 1/28* (2006.01)
*B01D 61/32* (2006.01)

(52) U.S. Cl.
CPC ......... *A61M 1/28* (2013.01); *A61M 1/282* (2013.01)
USPC .......... 210/97; 210/141; 210/143; 210/321.6; 210/321.65; 210/646; 604/29; 604/65; 700/273

(58) Field of Classification Search
CPC ............ A61M 1/28; A61M 2001/282; A61M 2001/284; B01D 61/32; B01D 61/30
USPC ................. 210/85–87, 96.1, 96.2, 141, 143, 210/321.65, 637, 645–647, 739, 929, 97, 210/321.6; 604/5.01, 6.01, 6.05, 6.09, 29, 604/65–67; 600/300; 700/19, 273; 702/273, 702/19; 705/2.3, 2, 3; 706/45–48, 924

See application file for complete search history.

(56) References Cited

U.S. PATENT DOCUMENTS

| | | | |
|---|---|---|---|
| 4,190,047 | A | 2/1980 | Jacobsen et al. |
| 4,370,983 | A | 2/1983 | Lichtenstein |
| 5,324,422 | A | 6/1994 | Colleran et al. |

(Continued)

FOREIGN PATENT DOCUMENTS

| | | |
|---|---|---|
| JP | 2003-047657 | 2/2003 |
| WO | 99/06082 | 2/1999 |

(Continued)

OTHER PUBLICATIONS

International Preliminary Report on Patentability issued Jan. 3, 2013 for corresponding Intl. Application No. PCT/US2011/048202.

(Continued)

*Primary Examiner* — Joseph Drodge  
(74) *Attorney, Agent, or Firm* — K&L Gates LLP

(57) ABSTRACT

The present system and method in one embodiment limit a maximum instantaneous peritoneal volume to a comfortable level, while allowing the dialysis machine to advance to fill a prescribed volume whenever the drain ends after a minimum drain percentage has been attained. If a low drain condition occurs, the nominal fill volume is lowered and a therapy cycle is added, so that a prescribed total amount of fresh therapy fluid is used during therapy, maximizing therapeutic benefit. An allowable residual volume at the end of an incomplete drain is increased, thereby lowering the probability of a subsequent low drain condition.

31 Claims, 10 Drawing Sheets

(56) References Cited

U.S. PATENT DOCUMENTS

| | | | |
|---|---|---|---|
| 5,334,139 | A | 8/1994 | Jeppsson et al. |
| 5,350,357 | A | 9/1994 | Kamen et al. |
| 5,421,823 | A | 6/1995 | Kamen et al. |
| 5,643,201 | A | 7/1997 | Peabody et al. |
| 5,670,057 | A | 9/1997 | Chen et al. |
| 6,074,359 | A | 6/2000 | Keshaviah et al. |
| 6,228,047 | B1 | 5/2001 | Dadson |
| 6,503,062 | B1 | 1/2003 | Gray et al. |
| 6,558,343 | B1 | 5/2003 | Neftel |
| 6,592,542 | B2 | 7/2003 | Childers et al. |
| 6,691,047 | B1 | 2/2004 | Fredericks |
| 6,836,175 | B2 | 12/2004 | Morikawa |
| 6,976,973 | B1 | 12/2005 | Ruddell et al. |
| 7,029,456 | B2 | 4/2006 | Ware et al. |
| 7,238,164 | B2 | 7/2007 | Childers et al. |
| 7,351,340 | B2 | 4/2008 | Connell et al. |
| 7,756,722 | B2* | 7/2010 | Levine et al. ............ 705/2 |
| 7,988,849 | B2* | 8/2011 | Biewer et al. ............ 210/94 |
| 8,142,649 | B2* | 3/2012 | Childers et al. .......... 210/87 |
| 8,182,673 | B2* | 5/2012 | Childers et al. .......... 210/141 |
| 8,197,439 | B2* | 6/2012 | Wang et al. .............. 604/67 |
| 8,500,676 | B2* | 8/2013 | Jansson et al. .......... 604/29 |
| 2003/0204162 | A1 | 10/2003 | Childers et al. |
| 2005/0256745 | A1 | 11/2005 | Dalton |
| 2007/0215545 | A1* | 9/2007 | Bissler et al. ............ 210/646 |
| 2008/0015493 | A1 | 1/2008 | Childers et al. |
| 2008/0161751 | A1 | 7/2008 | Plahey et al. |
| 2009/0036757 | A1 | 2/2009 | Brockway et al. |
| 2009/0113335 | A1* | 4/2009 | Sandoe et al. ............ 715/773 |
| 2009/0294339 | A1* | 12/2009 | Biewer et al. ............ 210/85 |
| 2010/0010427 | A1 | 1/2010 | Yu et al. |
| 2010/0137782 | A1* | 6/2010 | Jansson et al. .......... 604/28 |
| 2010/0191180 | A1 | 7/2010 | Childers et al. |
| 2010/0191181 | A1 | 7/2010 | Childers et al. |
| 2012/0029937 | A1* | 2/2012 | Neftel et al. ............ 705/2 |
| 2013/0184638 | A1* | 7/2013 | Scarpaci et al. .......... 604/28 |
| 2013/0317795 | A1* | 11/2013 | Akonur et al. .......... 703/2 |
| 2014/0221910 | A1* | 8/2014 | Mastalli et al. .......... 604/29 |

FOREIGN PATENT DOCUMENTS

| | | |
|---|---|---|
| WO | 01/64236 | 9/2001 |
| WO | 2004/009156 A2 | 1/2004 |
| WO | 2005/035023 | 4/2005 |

OTHER PUBLICATIONS

James C. Brandes, et al., "Optimization of Dialysate Flow and Mass Transfer During Automated Peritoneal Dialysis," American Journal of Kidney Diseases, vol. 25, No. 4, Apr. 1995, 9 pages.

Bengt Rippe, et al., "Computer simulations of peritoneal fluid transport in CAPD," Kidney International, vol. 40, (1991), pp. 315-325.

Edward Vonesh, et al., "Net Fluid Absorption Membrane Transport Models of Peritoneal Dialysis," Blood Purif., 1992, vol. 10, pp. 209-226.

Serena brochure visualizing prescription software, 2 pages.

Non-Final Office Action for U.S. Appl. No. 12/362,240 mailed Jul. 18, 2011.

Non-Final Office Action for U.S. Appl. No. 12/362,259 mailed Sep. 23, 2011.

\* cited by examiner

DRAIN AND FILL LOGIC FOR AUTOMATED PERITONEAL DIALYSIS

PRIORITY

This application claims priority to and the benefit as a non-provisional application of provisional U.S. Patent Application No. 61/384,001, entitled "Drain And Fill Logic For Automated Peritoneal Dialysis", filed Sep. 17, 2010, the entire contents of which is incorporated herein by reference and relied upon.

CROSS REFERENCE TO RELATED APPLICATIONS

This patent application is related in subject matter to commonly owned U.S. patent application Ser. No. 12/362,240 (2010/0191180), now U.S. Pat. No. 8,142,649, and Ser. No. 12/362,259 (2010/0191181), now U.S. Pat. No. 8,182,673, both of which were filed Jan. 29, 2009.

BACKGROUND

The present disclosure relates generally to peritoneal dialysis, and in particular to peritoneal dialysis systems useful in manipulating the number of cycles, drain volumes and fill volumes in a multiple cycle dialysis therapy.

Automated Peritoneal Dialysis ("APD") is a natural evolution of Continuous Ambulatory Peritoneal Dialysis ("CAPD"), in which the patient introduces the entire contents of a dialysate solution bag into his/her peritoneum and allows the volume to dwell for three to six hours. After the dwell period, the fluid is drained using gravity. The above process is typically repeated three or four times each day as necessary. Working adults may perform an exchange at home before leaving for work, one at work during their lunch hour, one when the patient arrives home from work and one just before the patient goes to bed. Some school-aged patients follow a similar routine except they perform their mid-day exchange at school.

APD machines (sometimes called "cyclers") perform sequential exchanges during the night when the patient is sleeping, making APD a more convenient therapy. Also, the treatment is carried out in the privacy of the patient's home, so that others do not have to know that the patient is undergoing dialysis treatment. It is no surprise that most patients prefer APD over CAPD.

However, there are some important differences between CAPD and APD. CAPD is typically performed with the patient sitting upright in a chair, whereas APD is typically performed with the patient lying down. The patient's internal catheter may work its way down into the bottom of the patient's peritoneal cavity (pelvic area) during the day when the patient is up and about so that it is not in an optimum position for draining when the patient is in a prone or sleeping position. Even with the catheter in the correct position, a supine or sitting position is generally better for draining than is the prone or sleeping position. Thus APD treatments can experience incomplete drains.

Continuous Cycling Peritoneal Dialysis ("CCPD") is one popular APD therapy because the therapy performs a full drain after every dwell, minimizing the potential for overfill due to the fluid that is ultrafiltered or removed from the patient's body. CCPD can however present a challenge when a patient does not drain well. In a night therapy, the patient likely does not want to be awakened every 1.5 hours or so to sit up and for a more complete drain.

Accordingly, CCPD therapy cyclers in some instances advance from drain to fill after a minimum percentage of the patient's previous fill volume has been drained, for example, when the drain flow rate has slowed to a point that time is being wasted that could be used for therapeutic benefit. An alarm will typically be posted if the drain flow rate slows to a certain rate before the minimum drain percentage has been exceeded. The HomeChoice/Pro® APD cycler, provided by the assignee of the present disclosure, is considered one of the best draining cyclers on the market, producing fewer alarms when compared to its competitors. Even still, low drain volume alarms occur.

An APD cycler with improved drain control is needed accordingly.

SUMMARY

The present disclosure sets forth systems and methods for performing a medical fluid treatment, such as peritoneal dialysis. In a preferred embodiment, the systems and methods operate with an automated periotoneal dialysis machine, such as a HomeChoice® machine marketed by the assignee of the present disclosure. The automated peritoneal dialysis machine includes a pump and one or more controller, processor, computer or memory (referred to herein collectively as a logic implementer or control unit) for operating the pump and other automated equipment of the machine. The machine also includes a user interface, e.g., including a video monitor and one or more input device, for entering information into the control unit.

The systems and methods of the present disclosure attempt to maximize therapy performance, patient comfort and patient safety. Regarding therapy performance, the systems and methods of the present disclosure seek to use all of the available prescribed therapy fluid or dialysate. By doing so, the systems and methods maximize performance by attempting to expend all of the osmotic gradient, which maximizes the therapy's ability to remove waste and toxins and also to remove excess water or ultrafiltrate ("UF") from the patient.

Regarding patient comfort and safety, the systems and methods can set a maximum allowable instantaneous peritoneal volume above which the systems and methods will not allow the patient's peritoneum to be filled. The maximum fluid volume that the patient's peritoneum has to hold occurs at the end of a dwell phase. The dwell phase occurs after a fill phase and prior to a drain phase, making up a cycle of the therapy. The fill phase adds an initial volume of fluid to the patient's peritoneum. If the previous drain phase does not result in a complete drain, the patient's peritoneum even prior to the fill will have a residual volume of fluid. At the end of the fill phase, then, the volume of fluid in the patient's peritoneum will include the residual drain volume plus the fill volume. Over the dwell phase an ultrafiltration volume is pulled from the patient and added to the residual drain volume and the fill volume already residing in the patient's peritoneal cavity. The systems and methods of the present disclosure ensure that the estimated peritoneal volume (the sum of the three volumes, residual drain, fill and ultrafiltration), does not exceed a maximum allowable peritoneal volume at the end of the dwell.

Further regarding patient comfort, the systems and methods of the present disclosure attempt to limit low drain alarms as much as possible. Automated peritoneal therapies often take place at night while the patient is sleeping. The APD machine of the present disclosure is provided with a low drain alarm that wakes the patient at the end of the drain phase if a certain minimum percentage of the estimated peritoneal volume at the end of dwell has not been drained from the patient.

Sometimes the patient can put himself or herself into a physical position when sleeping that is not conducive to draining well, e.g., the patient line becomes partially kinked or occluded. The drain alarm alerts the patient to reposition himself or herself, but in doing so, wakes the patient. Excessive drain alarms are not desirable and diminish the overall quality of the APD therapy and patient well-being.

The APD machine is configured in one embodiment to provide the patient, doctor or clinician initially with the option of running a continuous cycling peritoneal dialysis ("CCPD") therapy or a tidal therapy. Examples of suitable CCPD and tidal therapies for the APD machine and system of the present disclosure are set forth herein.

In one CCPD therapy embodiment of the system and method of the present disclosure, a minimum drain percentage is set to an initial level. Again, the minimum drain percentage is the minimum percentage of the estimated peritoneal volume at the end of dwell that needs to be drained over the drain phase to avoid a low drain alarm. The initial minimum drain percentage can be set by a doctor's prescription for example. Alternatively, the initial minimum drain percentage is set in the memory of the APD machine using an equation in which the minimum drain percentage is determined by adding the fill volume per cycle to the expected UF per cycle and dividing that sum by the prescribed maximum peritoneal volume. A typical initial minimum drain percentage can for example be between seventy and eighty-five percent.

In another alternative embodiment, the low drain alarm threshold is determined by a second equation which determines a threshold volume called the maximum residual volume, below which the estimated peritoneal volume must be reduced to avoid a low drain alarm. A corresponding equation is given by subtracting the fill volume per cycle and the expected UF per cycle from the maximum peritoneal volume. The resulting maximum residual volume is then set to a level such that a subsequent fill and ultrafiltrate ("UF") dwell volume will not exceed the maximum peritoneal volume.

If the initial minimum drain percentage is not achieved at the end of one of the drain phases, the CCPD system and method, instead of posting an alarm and waking the patient: (i) add an additional fill, dwell and drain cycle; (ii) divide the remaining total volume of fresh dialysate left to deliver to the patient by n+1 remaining cycles instead of just n cycles thus lowering the amount of the fill volume for each n+1 remaining fill phase; (iii) lower the amount of expected UF for each dwell phase, where the expected UF can be taken to be a percentage (e.g., eight percent) of the reduced fill volume per phase as opposed to the same percentage of the previous non-reduced fill volume per phase; and (iv) calculate a new lower minimum drain percentage by adding the new fill volume per cycle to the new expected UF per cycle and dividing that sum by the prescribed maximum peritoneal volume. Or alternatively, a new maximum residual volume is calculated by subtracting the new fill volume per cycle and the new expected UF per cycle from the prescribed maximum peritoneal volume.

If the actual drain volume or percentage, which did not meet the initial drain percentage and caused a cycle to be added, now meets the new lowered drain percentage, therapy proceeds with the additional n+1 amount of cycles, the new fill volume per cycle, the new expected UF per cycle and the new minimum drain percentage of each remaining drain. If the total prescribed therapy time is important, and is set as a parameter not to be exceeded, then the dwell period for each of the remaining n+1 dwell phases is lessened so that the original, prescribed total therapy time is not exceeded despite the added cycle. If the total prescribed therapy time is not as important, and is not set as a parameter to hold constant, then the dwell periods can remain unchanged or be shortened by a lesser amount, such that the total therapy time is extended.

If the actual drain percentage, which did not meet the minimum drain percentage and caused a cycle to be added, still does not meet the newly determined, lowered minimum drain percentage, the system and method add a second additional cycle to further lower the fill volume per cycle, the expected UF per cycle and thus the minimum drain percentage per the equation discussed above. This sequence is continued until the actual drain percentage meets at least the minimum drain percentage.

In an alternative CCPD therapy embodiment, the system and method of present disclosure, instead of dividing the remaining total volume of fresh dialysate left to deliver to the patient by the n+1 remaining cycles, set the new fill volume to a new nominal or average value. For example if the total volume of fresh dialysate to deliver to the patient over the entire therapy is 12,000 milliliters, and the initial number of cycles is four, the initial nominal fill volume per cycle is 3,000 milliliters. When an additional fifth cycle is added due to an insufficient drain, the nominal fill volume per cycle now becomes 2,400 milliliters. The new nominal fill volume per cycle is then set as the fill volume even though the previous one or more fill used 3,000 milliliters. The result is that the last cycles fill will be shortened to whatever amount of fresh solution is allowable. It should thus be appreciated that here too, all the fresh solution is used to maximize therapeutic benefit.

The system and method in an embodiment set a separate extra-low drain threshold, which causes an alarm to be posted, so as to wake the patient when some form of serious flow obstruction is obviously taking place. That is, when the actual drain is so small that the low drain is clearly not due to the patient's inability to drain, the system and method in such case wake the patient in one implementation. It should be apparent however that the present system and method at least attempt to limit low drain alarms and the associated waking of the patient a good extent.

The above-described procedure can be performed at multiple, different times over the course of therapy, stepping down the minimum drain percentage when needed. The system and method, by making the minimum drain percentage a fraction of the maximum allowable peritoneal volume, hold that volume as an asymptote that is not surpassed. Also, because the minimum drain percentage calculation takes into account the remaining fill volume remaining to deliver to the patient, e.g., the nominal fill volume, the system and method ensure that the patient uses all of the prescribed therapy volume of fresh dialysate over the course of therapy, which in turn maximizes the therapeutic benefit.

The CCPD systems and methods discussed above are in one embodiment initiated automatically upon the APD machine's detection of a low drain volume/percentage. In an alternative embodiment, the CCPD systems and methods are provided as options to the patient. In this alternative embodiment, the CCPD therapy can run according to prescription until a low drain volume/percentage issue occurs, at which time the APD machine wakes the patient. The patient is requested to attempt to correct the incomplete drain. The patient is then provided with an option of continuing the therapy according to the initial prescription or to change to a modify minimum drain volume/percentage mode. If the patient feels that the therapy can proceed as initially prescribed without a further drain issue, wants to be given the chance to complete the drain if another low drain situation arises and/or for any other reason, the patient can continue the CCPD therapy as initially prescribed. Alternatively, if the patient feels like the minimum drain percentage/volume is currently set too high based on how the patient is draining and/or for any other reason, the patient can enter the modify minimum drain volume/percentage mode, which operates according to one of the embodiments set forth herein in an attempt to prevent further low drain alarms, while maintaining patient safety, comfort and therapy effectiveness.

In one suitable tidal therapy embodiment, the system and method of the present disclosure begins with a CCPD therapy, which can be a CCPD therapy already stored in the memory of the APD machine. The tidal therapy system and method automatically modify the selected CCPD therapy into a tidal therapy based on a selection by the patient, nurse or clinician to add just one additional cycle or alternatively to add two additional cycles (or more if desired). If only one additional cycle is added, the selected CCPD therapy is modified to leave a first residual volume (e.g., 25% of initial fill) in the patient's peritoneal cavity at the end of each normal cycle, excluding the last cycle in which the patient can perform a complete drain. If two additional cycles are chosen to be added, the residual drain volume is set to a higher level, e.g., 40% of the initial fill. In either case, the prescribed residual drain volumes help the patient to avoid low drain alarms.

As discussed in detail below, knowing the desired residual volume and the number of cycles to be added, the tidal therapy is derived automatically from the selected CCPD therapy, so as to: (i) deliver the same total amount of fresh dialysis solution to the patient over all of the cycles as is done in the selected CCPD therapy, (ii) ensure that the patient is filled to the same level after each fill phase (taking into account either fresh dialysis fluid only for the first fill phase or a combination of fresh dialysis fluid and the residual drain volume for the fill phases occurring after the first fill phase) as is filled in each phase of the selected CCPD therapy, and (iii) ensure that the tidal therapy has the same total therapy duration as the selected CCPD therapy. In performing the automatic conversion from CCPD to tidal therapy, the dwell duration is reduced to a first amount for the "plus one" tidal therapy and is reduced further to a second amount for the "plus two" therapy, and so on if additional cycles are added.

The tidal therapy just described is therefore readily programmed. The patient uses the "plus one" or "plus two" version based upon whether the patient, doctor or clinician believes that the lesser residual drain volume of the "plus one" cycle tidal therapy will avoid a low drain condition or whether the patient, doctor or clinician believes that the higher residual drain volume of the "plus two" cycle tidal therapy is needed. Once chosen, the APD machine automatically programs itself to run a tidal therapy based upon the selected underlying CCPD therapy.

It is accordingly an advantage of the present disclosure to provide a peritoneal dialysis system and method that attempt to ensure that a prescribed total volume of fresh dialysate is delivered to the patient over the course of therapy.

It is another advantage of the present disclosure to provide a peritoneal dialysis system and method that ensure that a therapeutic benefit is maximized.

It is a further advantage of the present disclosure to provide a peritoneal dialysis system and method that ensure that a maximum allowable peritoneal volume is not exceeded.

It is yet a further advantage of the present disclosure to provide a peritoneal dialysis system and method that limit the waking of the patient due to low drain alarms during therapy.

It is still another advantage of the present disclosure to provide a peritoneal dialysis system and method that maintain a prescribed total time for therapy.

It is still a further advantage of the present disclosure to provide a peritoneal dialysis system and method in which the patient is provided with an option to continue with a prescribed therapy or to allow the APD machine to modify the prescribed therapy in an attempt to avoid further low drain alarms.

Further still, it is an advantage of the present disclosure to provide the patient, nurse or doctor with a choice between running a continuous cycling peritoneal dialysis therapy or a tidal therapy.

Yet another advantage of the present disclosure is to provide the nurse or doctor with a method of automatically converting a continuous cycling peritoneal dialysis ("CCPD") therapy to a tidal peritoneal dialysis therapy, which maintains equivalent therapy volumes and durations.

Additional features and advantages are described herein, and will be apparent from the following Detailed Description and the figures.

DETAILED DESCRIPTION

Dialysis System Generally

Figure 1:
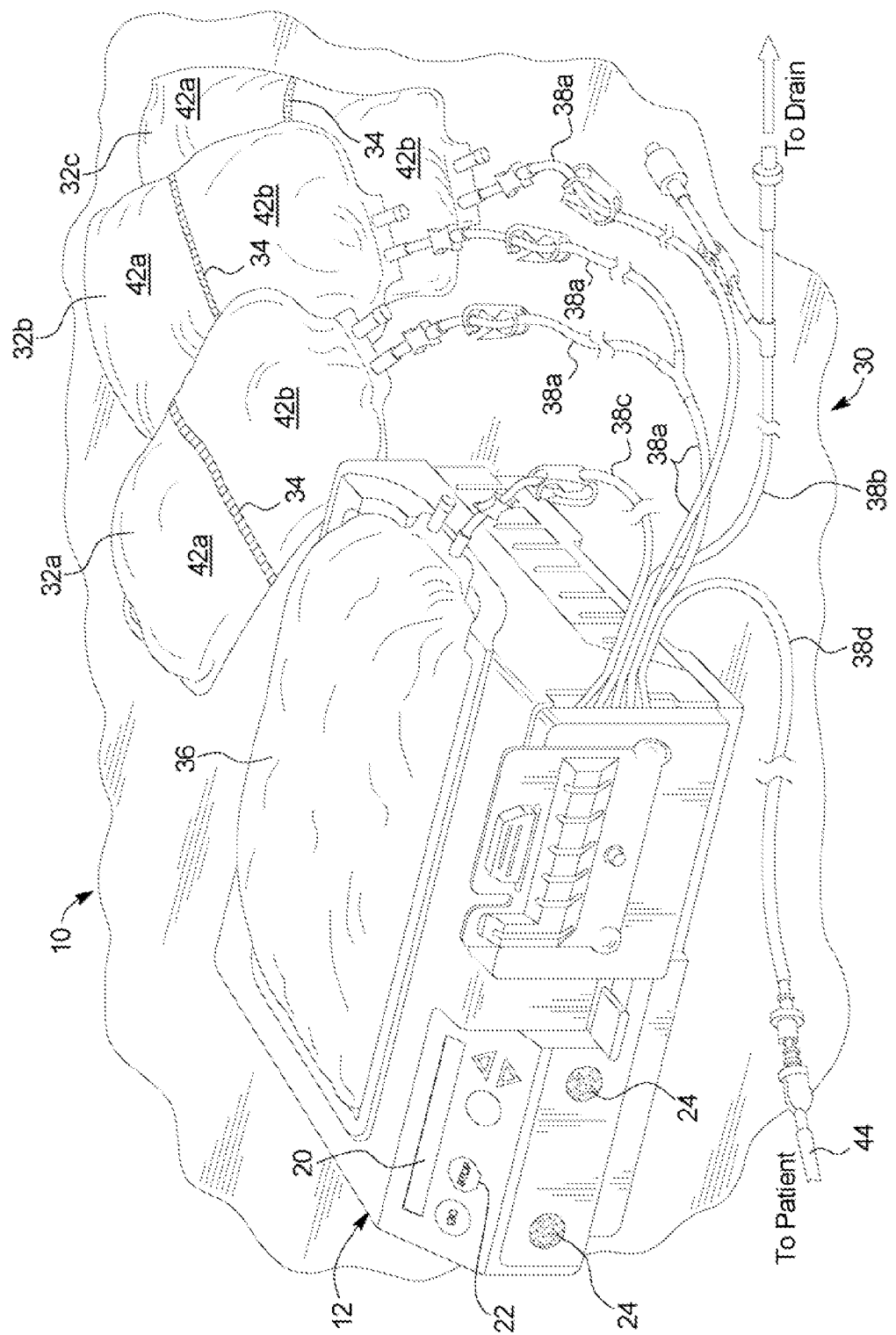
FIG. 1 is a perspective view of one embodiment of a dialysis system having a self-regulating drain logic according to the present disclosure.
Figure 2:
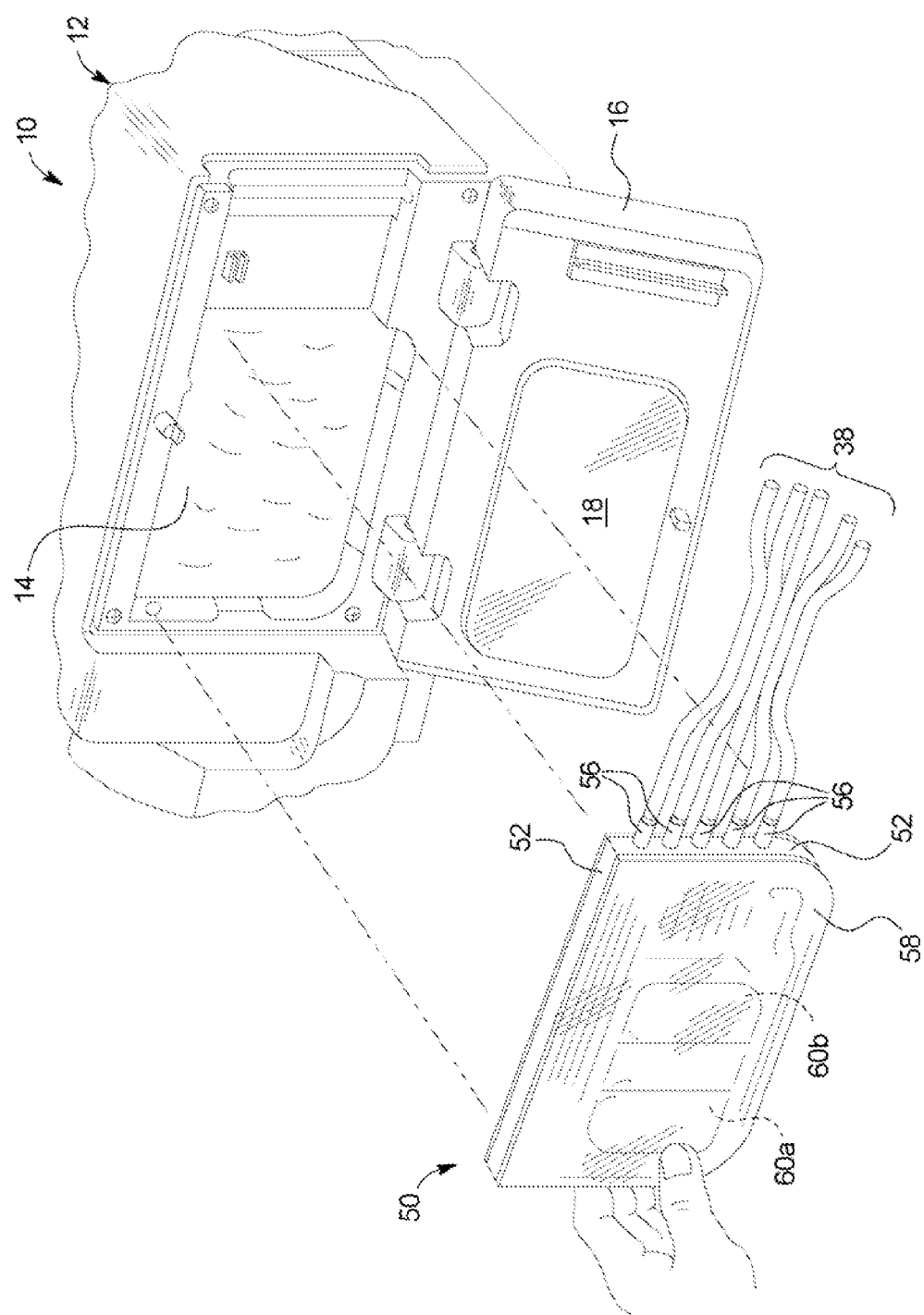
FIG. 2 is a perspective view of one embodiment of a disposable cassette operable with a dialysis system having a self-regulating drain logic according to the present disclosure.

Referring now to the drawings and in particular to FIGS. 1 to 2, a renal failure therapy system 10 is provided. System 10 is applicable generally to any type of automated peritoneal dialysis ("APD") system. System 10 in the illustrated embodiment includes a dialysis instrument 12. Dialysis instrument 12 is configured for the type of APD therapy system provided. Dialysis instrument 12 includes a central processing unit ("CPU") and memory, and may include one or more additional processor and memory (e.g., safety, valve, heater, pump, video and audio (e.g., voice guidance) controllers) operable with the CPU, the totality of which may be called a logic implementer or control unit. The logic implementer operates with a user interface ("UI"), such as a graphical user-machine interface ("GUI"), e.g., via a video controller component of the logic implementer. The GUI includes a video monitor 20 and one or more types of input devices 22, such as a touch screen or electromechanical input device (e.g., a membrane switch). The CPU is also configured to receive instructions and/or data from the GUI, a remote memory storage device, an internet or database connection and/or a wirelessly connected device.

The logic implementer in cooperation with video monitor 20 provides therapy instructions and setup confirmation to the patient or caregiver visually via characters/graphics. For example, characters/graphics can be displayed (i) to provide instructions regarding placement of a distal end of the patient line onto instrument 12 (discussed below) for priming and/or (ii) to inform the patient when the patient line has been primed fully. Additionally or alternatively, a voice guidance controller of the logic implementer in cooperation with speakers 24 provides (i) and/or (ii) listed above.

As seen in FIG. 1, dialysis instrument 12 accepts and operates with a disposable set 30. Disposable set 30 includes one or more supply bag 32a to 32c (referred to herein collectively as supply bags 32 or individually, generally, as supply bag 32), shown here as dual-chamber supply bags separating two fluids via a peel or frangible seal 34. Disposable set 30 also includes a drain bag (not illustrated), a warmer bag 36, and tubes 38a to 38d (referred to herein collectively as tubing or tubes 38 or individually, generally, as tube 38) and a disposable pumping/valve cassette 50 (FIG. 2).

Warmer bag 36 is used in a batch heating operation, in which the top of instrument 12 batch heats fluid within bag 36. System 10 can also pump spent fluid to a house drain, such as a bathtub, a toilet or sink, instead of to a drain bag, in which case the drain bag is not needed.

While three supply bags 32 are shown, system 10 can employ any suitable number of supply bags. Supply bags 32 are shown having multiple chambers 42a and 42b, separated by frangible seal 34, which hold different solutions depending on the type of therapy employed. For example, chambers 42a and 42b can hold buffer and glucose for an overall PD dialysate having a desired glucose level. Supply bags 32 are alternatively single chamber bags, which hold a single premixed solution, such as premixed PD dialysate having a desired glucose level.

As seen in FIGS. 1 and 2, a disposable cassette 50 connects to supply bags 32, drain bag and warmer bag 36 via tubes 38a, 38b and 38c, respectively. Tube 38d runs from cassette 50 to a patient connection 44. Cassette 50 in one embodiment includes a rigid structure having rigid outer walls 52 and a middle, base wall (not shown) from which pump chambers (60a and 60b as shown in FIG. 2), valve chambers (e.g., volcano valve chambers) and rigid fluid pathways extend. Rigid fluid ports 56 extend from a side wall 52 and communicate fluidly with the rigid cassette pathways and connect sealingly to tubing 38. Tubing 38 can be fixed to ports 56, in which case the bags 32 are spiked to allow fluid from the bags to flow through tubing 38 into cassette 50. Alternatively, tubing 38 is fixed to bags 32, in which case ports 56 or the mating tubing ends are spiked to allow fluid from the bags 32 and tubing 38 into cassette 50.

A pair of flexible membranes or sheets 58 (only one shown) is sealed to outer rigid walls 52 of the cassette. Cassette 50 is sealed within instrument 12 such that sheeting 58 forms the outer surfaces of the rigid fluid pathways of the hard cassette body. One of the sheets is moved to pump fluid through pump chambers (60a and 60b) and to open and close the cassette valves.

Instrument 12 can actuate the pump and valve chambers of cassette 50 pneumatically, mechanically or both. The illustrated embodiment uses pneumatic actuation. The HomeChoice® APD system, marketed by the assignee of the present disclosure, uses a pneumatic system described for example in U.S. Pat. No. 5,350,357 ("the '357 patent"), the entire contents of which are incorporated herein by reference and relied upon. As seen in FIG. 2, instrument 12 includes a flexible membrane 14, which creates different sealed areas with cassette sheeting 58 at each of the pump and valve chambers of cassette 50. Membrane 14 moves with the sheeting 58 in those areas to either open/close a valve chamber or pump fluid through (into and out of) a pump chamber. A cassette interface plate (not shown) is located behind membrane 14 and includes first and second chamber halves (not shown) that mate with chamber halves 60a and 60b of cassette 50 to form a pair of fixed volume pump chambers.

Instrument 12 in the illustrated embodiment includes a door 16, which closes against cassette 50. Door 16 includes a press plate 18, which can be operated mechanically (e.g., via the closing of the door) and/or pneumatically (e.g., via an inflatable bladder located in the door behind the press plate). Pressing plate 18 against cassette 50 in turn presses cassette 50 against pumping membrane 14, which cooperates with sheeting 58 of cassette 50 to pump fluid through chambers 60a and 60b and to open and close the cassette valve chambers.

The cassette interface plate located behind membrane 14 is configured to apply positive or negative pressure to the cooperating membrane 14 and cassette sheeting 58 at the different valve and pump areas. For example, positive pressure is applied to membrane 14/sheeting 58 at areas of the membrane/sheeting located within the rigid internal walls of cassette 50 that define pump chambers 60a and 60b to push fluid out of the pump chambers and within the chamber halves of the interface plate (not shown). Negative pressure is applied to membrane 14/sheeting 58 at those same areas to pull fluid into the pump chambers. Likewise, positive pressure is applied to membrane 14/sheeting 58 at areas of the sheeting within the rigid internal walls of cassette 50 and the interface plate defining the valve chambers to close outlet ports of the valve chambers. Negative pressure is applied to membrane 14/sheeting 58 at those same areas to open the outlets of the valve chambers.

U.S. Pat. No. 6,814,547 ("the '547 patent"), assigned to the assignee of the present disclosure, discloses a pumping mechanism in connection with FIGS. 17A and 17B and associated written description, incorporated herein by reference and relied upon, which uses a combination of pneumatic and mechanical actuation. FIGS. 15, 16A and 16B of the '547 patent and associated written description, incorporated herein by reference and relied upon, teach the use of mechanically actuated valves. One or both of these mechanisms can be used instead of the purely pneumatic system of the HomeChoice® machine.

The '357 patent and the '547 patent also teach different systems and methods, incorporated herein by reference and relied upon, of knowing and controlling the amount of fresh dialysate delivered to the patient, the amount of effluent dialysate removed from the patient, and thus the amount of additional fluid or ultrafiltrate ("UF") removed from the patient. UF is the blood and tissue water that the patient accumulates between treatments due to the patient's failed kidneys. The dialysis treatment removes this blood and tissue water as UF in an attempt to bring the patient back to his or her "dry weight". Either of the UF control systems and methods of the '357 patent and the '547 patent can be used as described below for controlling the fill and drain volumes according to the methods of system 10.

Another machine particularly well-suited to employ the self-regulating drain logic system and method of the present disclosure is disclosed in published Patent Cooperation Treaty applications WO 2009094179, WO 2009094183, WO 2009094185, WO 2009094182, WO 2009094184, and WO 2009094186, the entire contents of each of which are incorporated herein by reference and relied upon.

Drain and Fill Logic for Automated Peritoneal Dialysis

It is contemplated that when the patient initiates therapy at machine 12 of system 10, that system 12 provides the patient with different therapy modality options. These modality options can be selected using video screen 20 and/or speakers 24 and input device 22 on a therapy by therapy (e.g., daily) basis, such that modality options can be performed alternatively or otherwise be intermixed. System 10 can be configured such that the doctor or the patient selects the therapy modality profile to be performed. If selected by the doctor (nurse or clinician), the therapy modality profile can be downloaded to machine 12 via an internet or data network linked to APD machine 12 or be stored on a memory device, such as a flash drive or universal serial bus ("USB") drive, and plugged into a port of machine 12 in communication with the logic implementer of APD machine 12.

It is contemplated for system 10 to provide to the patient, clinician or doctor at least one continuous cycling peritoneal dialysis ("CCPD") modality option and at least one tidal therapy modality option. In general, a CCPD therapy attempts to completely drain the patient after each cycle, while a tidal therapy leaves a preset amount of dialysate in the patient at the end of each drain except the final drain (residual drain volume) and then fills the patient with a lesser preset amount of fresh solution on the following fill except for the first fill, which usually occurs after a full drain or otherwise when the patent is or near completely empty.

Figure 8:
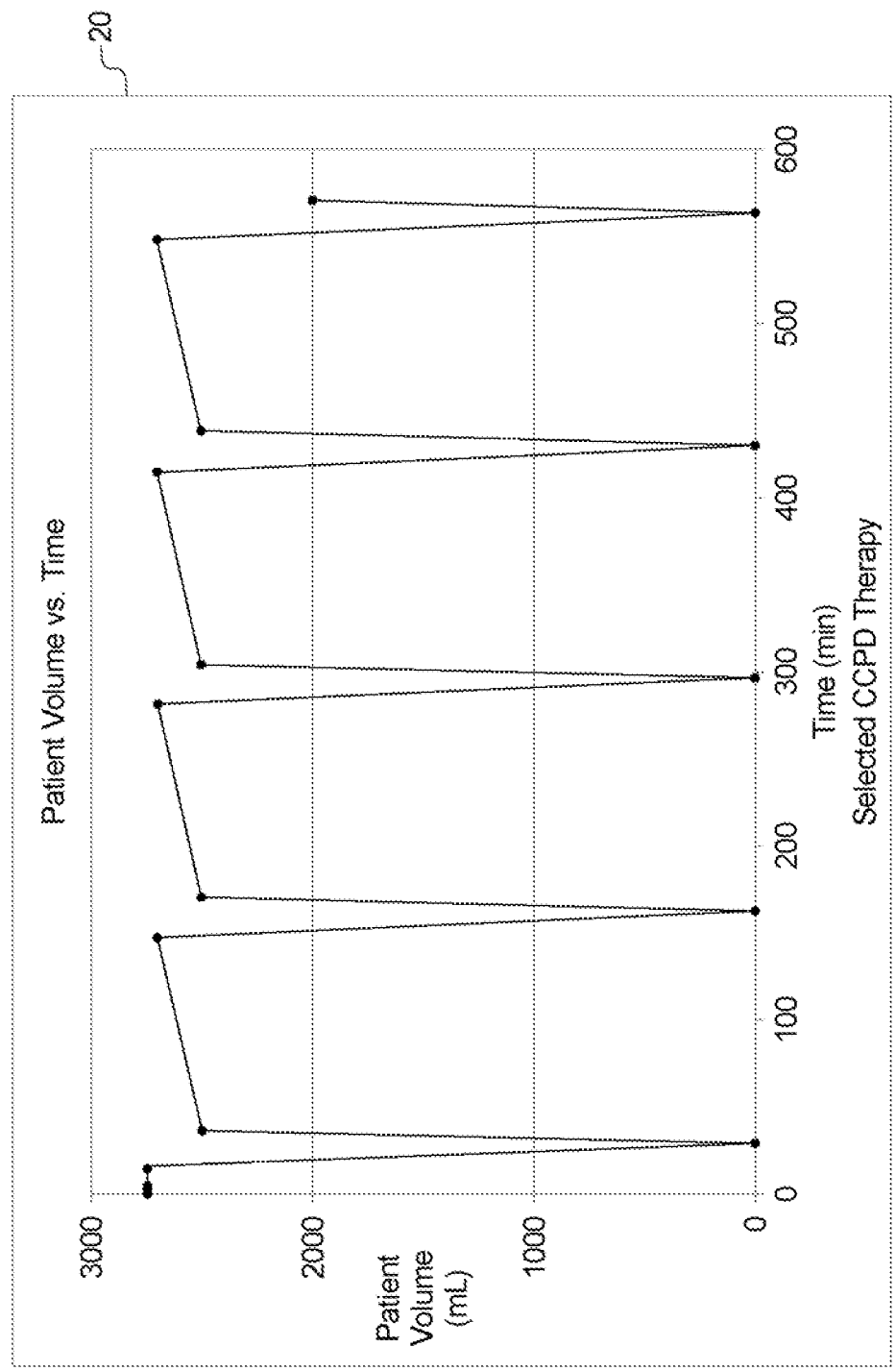
FIGS. 8 to 10 illustrate one embodiment for a tidal therapy method or algorithm of the present disclosure.
Figure 9:
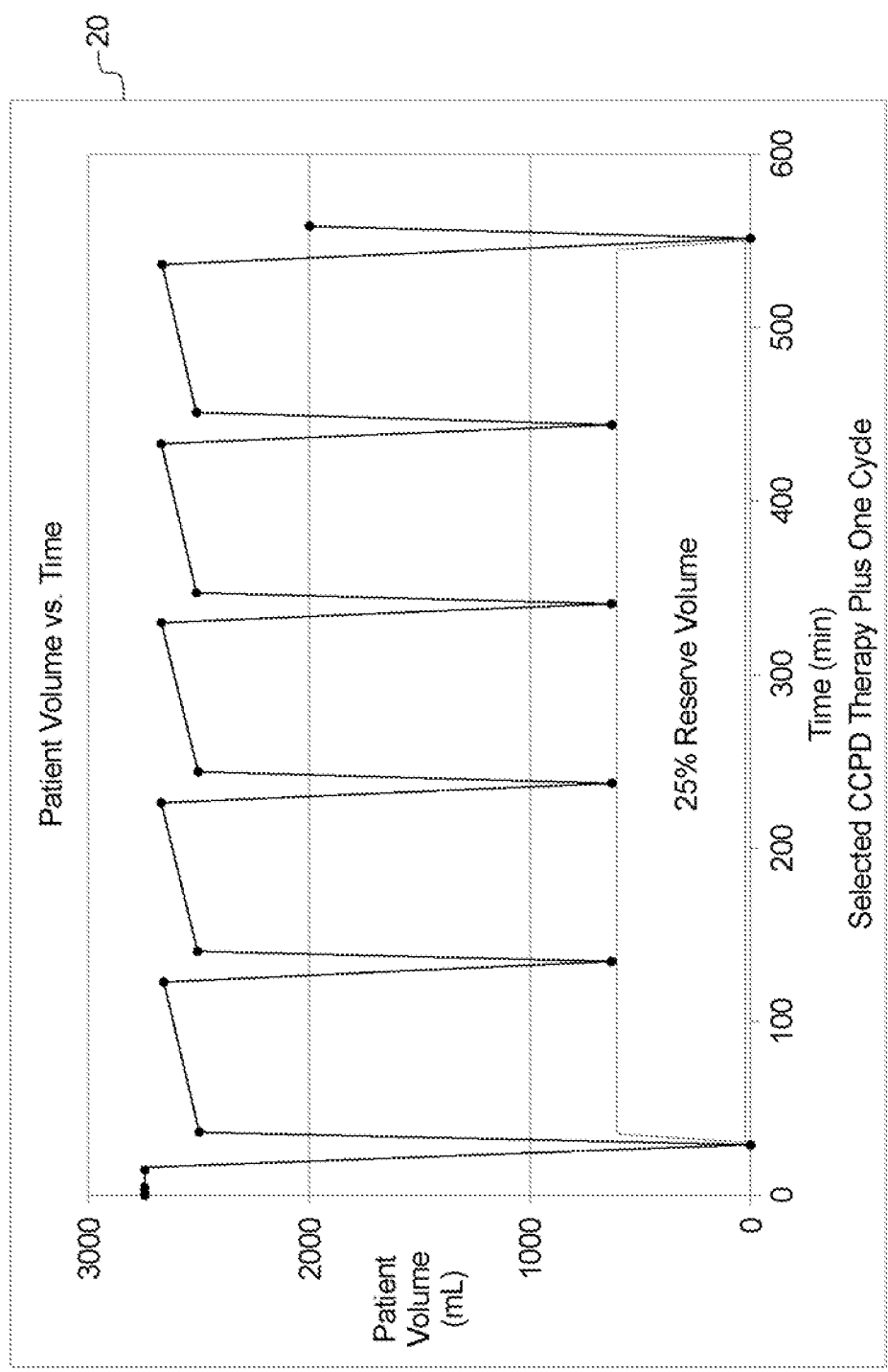
Figure 10:
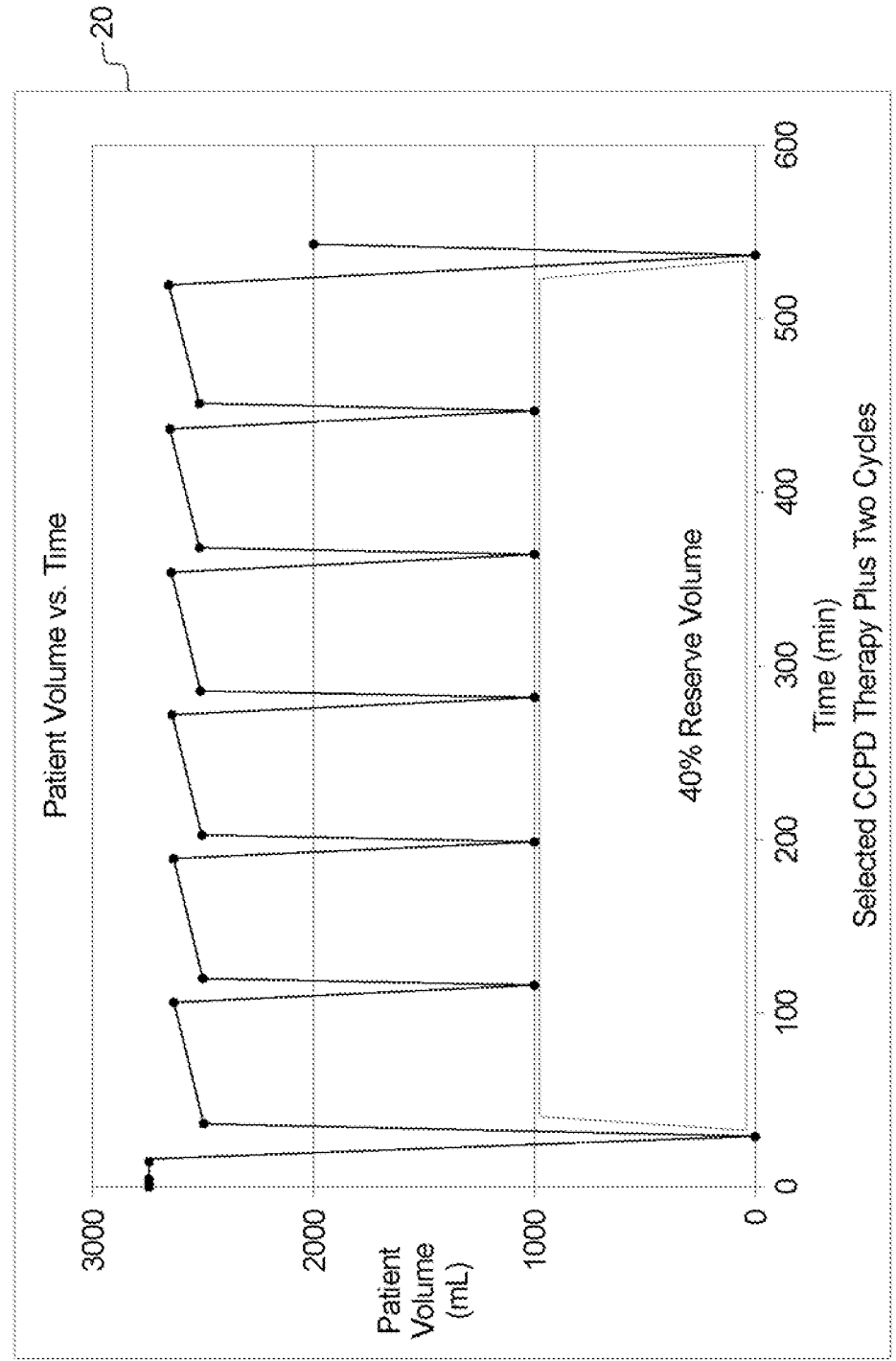

FIGS. 3 to 7 illustrate various embodiments for a CCPD therapy for system 10 that can be modified to be a pseudo-tidal therapy if the patient is experiencing incomplete drains. FIGS. 8 to 10 illustrate embodiments for tidal therapies for system 10.

1. CCPD Therapies

Figure 3:
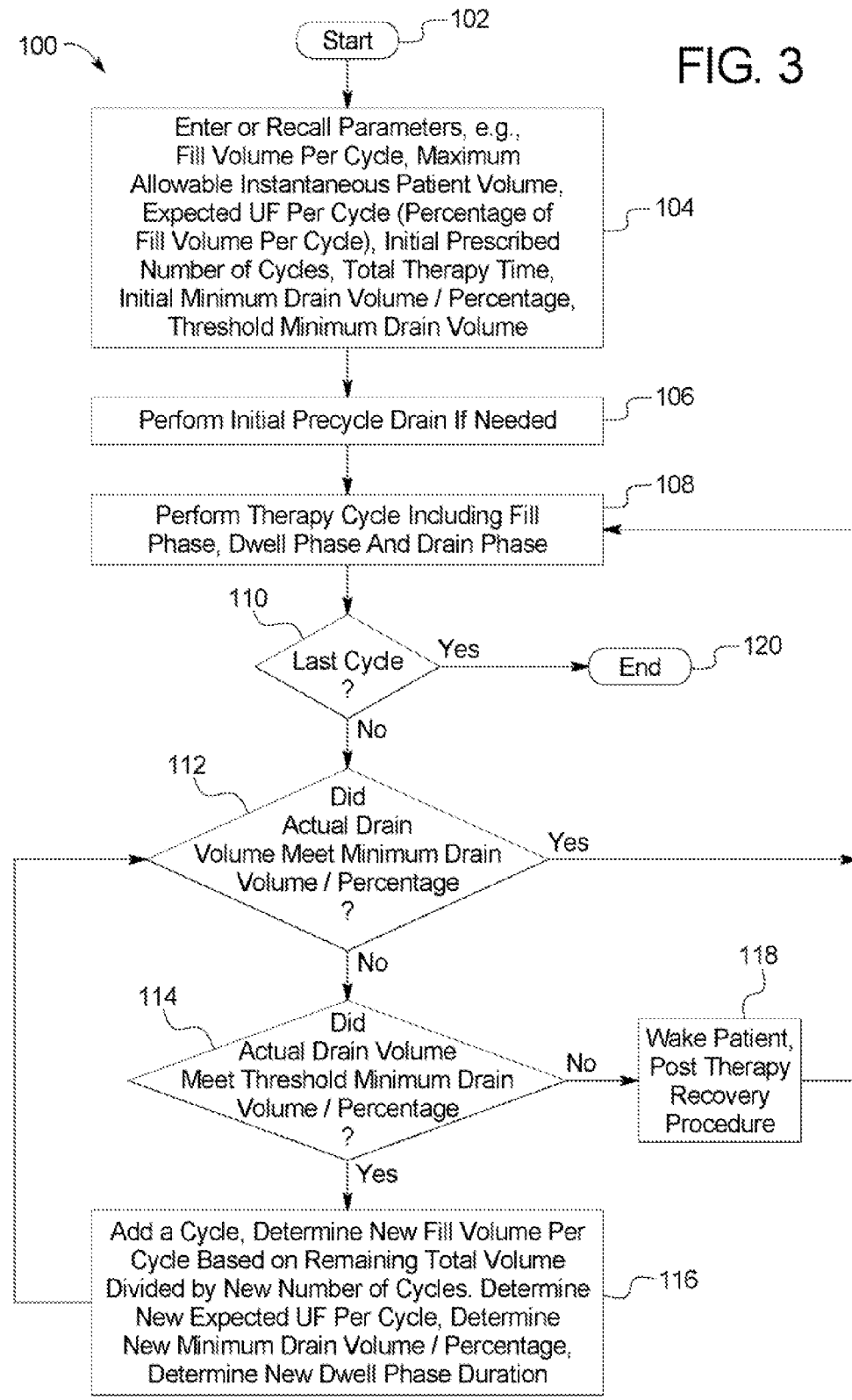
FIG. 3 is a logic flow diagram illustrating one continuous cycling peritoneal dialysis ("CCPD") therapy method or algorithm of the present disclosure.

Referring now to FIG. 3, method 100 illustrates one possible CCPD method or algorithm for implementation into the control unit or logic implementer of APD machine 12. As a CCPD therapy, method 100 attempts to completely drain the patient after each cycle. As seen below, if the patient experiences low drain conditions, (i) the patient can be provided the option to, or (ii) the machine can automatically, lower the required minimum drain volume or percentage and thus increase the patient's allowable residual drain volume in an effort to allow therapy to continue without further alarm even if the patient experiences further draining issues.

Method 100 begins at oval 102. At block 104, method 100 allows a doctor, nurse, clinician or patient to enter or recall an initial prescribed fill volume, which multiplied by an initial prescribed number of cycles, each cycle having a fill phase, dwell phase and drain phase, leads to a prescribed total sum of dialysis fluid volume that is to be delivered to the patient. The prescribed total sum of dialysis fluid volume of the fill phases that is to be delivered to the patient in an embodiment is the total volume delivered to the patient over the normal therapy cycles and does not include a last fill volume that is delivered to the patient after the cycles have been completed. The last fill volume resides within the patient after the patient disconnects from APD machine 12 and is removed at either a midday exchange or at night before the next set of normal therapy cycles is begun.

In one embodiment, the patient before each therapy (at block 104) enters the initial fill volume, which is presumed to be the volume for the fill phases of each of the prescribed cycles. The patient also before each therapy enters the last fill volume.

Besides the initial prescribed fill volume and/or prescribed total sum of dialysis fluid volume of the fill phases, method 100 allows the doctor, nurse, clinician or patient to enter or recall an expected UF volume per cycle, a maximum allowable peritoneal volume, an initial minimum drain volume, optionally a threshold minimum drain volume, an initial number of therapy cycles and optionally a total therapy time, as seen at block 104. The expected UF volume per cycle can be a percentage multiplied by the fill volume per cycle, e.g., eight percent multiplied by the fill volume. The percentage can be optimized for the patient given the patient's transport characteristics. It is therefore contemplated for the doctor, nurse, clinician or patient to enter the optimized UF percentage for the patient, e.g., one time for multiple treatments, such that the expected UF volume can be recalculated whenever the fill volume changes. Block 104 therefore indicates that the expected UF volume can be recalled from memory of APD machine 12 under normal circumstances (and not reentered by the patient for each treatment) and updated, e.g., by the doctor, nurse, clinician or patient, periodically after the patient's transport characteristics have been reevaluated.

The maximum allowable instantaneous peritoneal volume is the maximum amount of liquid that may reside at any one time within the patient's peritoneum. This generally occurs at the end of a dwell phase of a cycle, just before the ensuing drain phase is begun. The maximum allowable peritoneal volume can be the sum of three different liquid volumes. First, it includes the fill volume entered during the fill phase of a cycle. Second, it includes the UF volume that is pulled into the patient's peritoneum over the course of the dwell phase due to the osmotic gradient provided by the dialysate. Third, maximum allowable peritoneal volume can also include a residual drain volume due to an incomplete drain during the previous drain phase. Incomplete drains occur naturally because patients pocket fluid, such that a drain that is supposed to be a drain-to-empty will not remove all of the previous fill volume. Regardless of how much the three components contribute to the combined instantaneous peritoneal volume, method 100 does not allow the instantaneous peritoneal volume to exceed the maximum allowable peritoneal volume. It should be appreciated then that better patient drains allow for more fresh solution and more UF to be generated accordingly.

The maximum allowable peritoneal volume, like the expected UF volume/UF percentage, can be optimized for the patient. Here, optimization is generally based on the patient's size and comfort level regarding tolerance to liquid residing in, and creating pressure within, the patient's peritoneum. It is again contemplated for the doctor, nurse, clinician or patient to enter the maximum allowable peritoneal volume one time for multiple therapies. Block 104 therefore indicates that the maximum allowable peritoneal volume can be recalled from memory of APD machine 12 under normal circumstances (and not reentered by the patient for each treatment) and updated, e.g., by the doctor, nurse, clinician or patient, periodically after the patient has been reevaluated.

The initial minimum drain volume or drain percentage is in one embodiment the minimum amount of the fill volume and expected UF that needs to be drained to allow therapy to proceed as prescribed. The initial minimum drain volume or drain percentage in one embodiment is set high enough that therapy can proceed through the prescribed number of cycles without the patient's instantaneous peritoneal volume ever exceeding the maximum allowable peritoneal volume despite the fact that each drain may leave a residual volume in the patient before each subsequent fill phase. For example, the initial minimum drain percentage can be set to be 85% of the prescribed fill volume plus expected UF. Because the initial minimum drain percentage takes into account only 85% of the prescribed fill volume plus expected UF, residual drain volumes will add a step component to each cycle, such that the instantaneous peritoneal volume at the end of each dwell will increase over each cycle (see FIGS. 4 to 6). However, the initial minimum drain percentage is set high enough that even at the end of the dwell period of the last cycle, and assuming the patient just meets the minimum drain requirement in each cycle, the instantaneous peritoneal volume will not exceed the maximum allowable peritoneal volume, and thus will not tax the patient's comfort level.

The patient is typically awake for the drain phase of the final cycle, which can be set to occur in the morning as the patient is waking from sleep. The patient is therefore able to move about and drain all or virtually all of the peritoneal volume including the volume that has built over the course of treatment. System 10 and method 100 contemplate that the patient may shift during sleep, such that the patient's indwelling catheter is not located at an optimal position for dwell. The initial minimum drain volume or drain percentage is generally determined empirically and 85% is thought to be a good starting point. It is again contemplated for the doctor, nurse, clinician or patient to enter the initial minimum drain volume or drain percentage into the memory of the machine once for multiple treatments. Block 104 therefore indicates that the maximum allowable peritoneal volume can be recalled from the memory of APD machine 12 under normal circumstances (and not reentered by the patient for each treatment) and updated, e.g., by the doctor, nurse, clinician or patient, periodically after the patient has had obtained therapy experience with APD machine 12.

Figure 4:
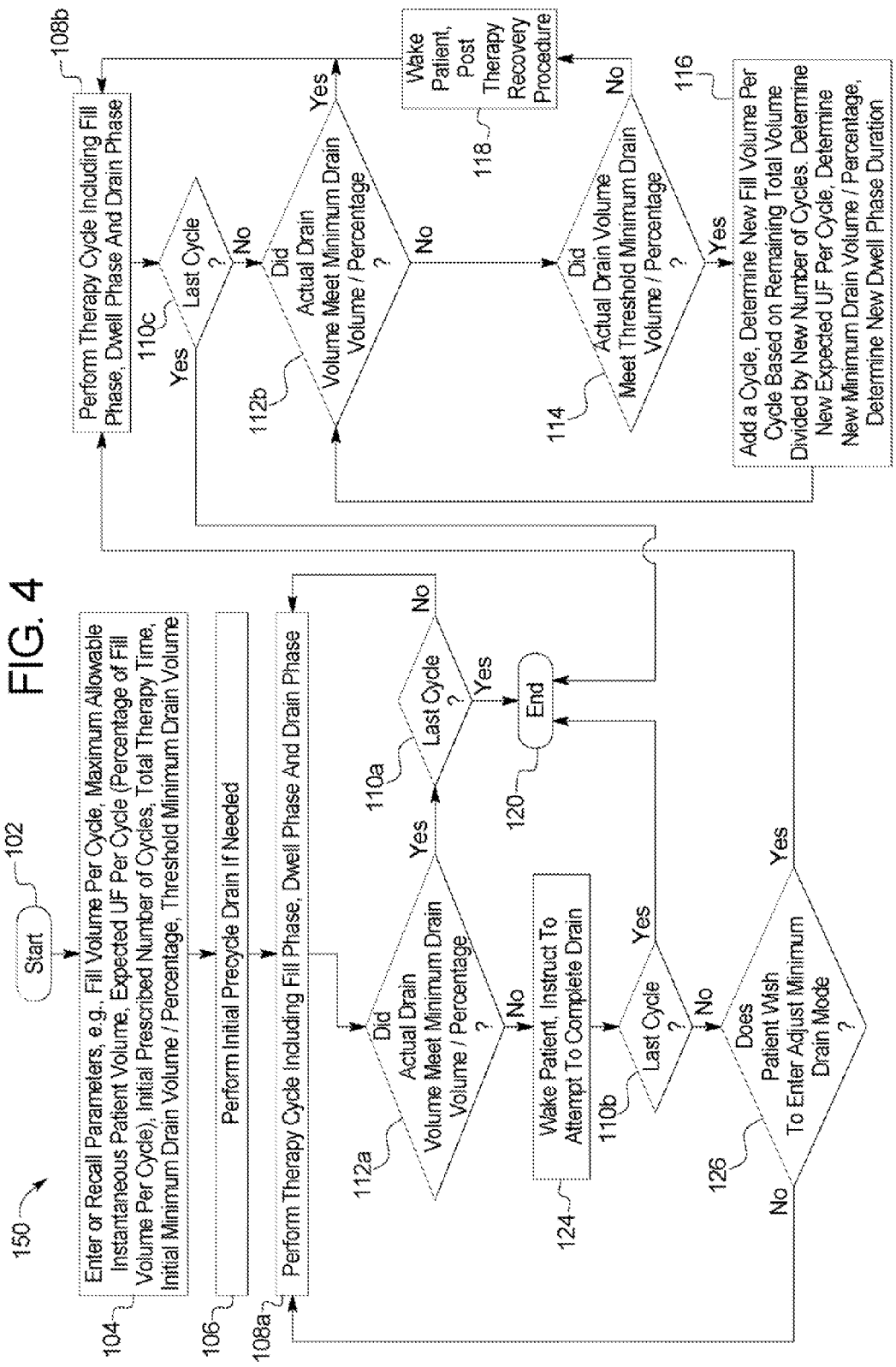
FIG. 4 is a logic flow diagram illustrating another CCPD method or algorithm of the present disclosure.
Figure 5:
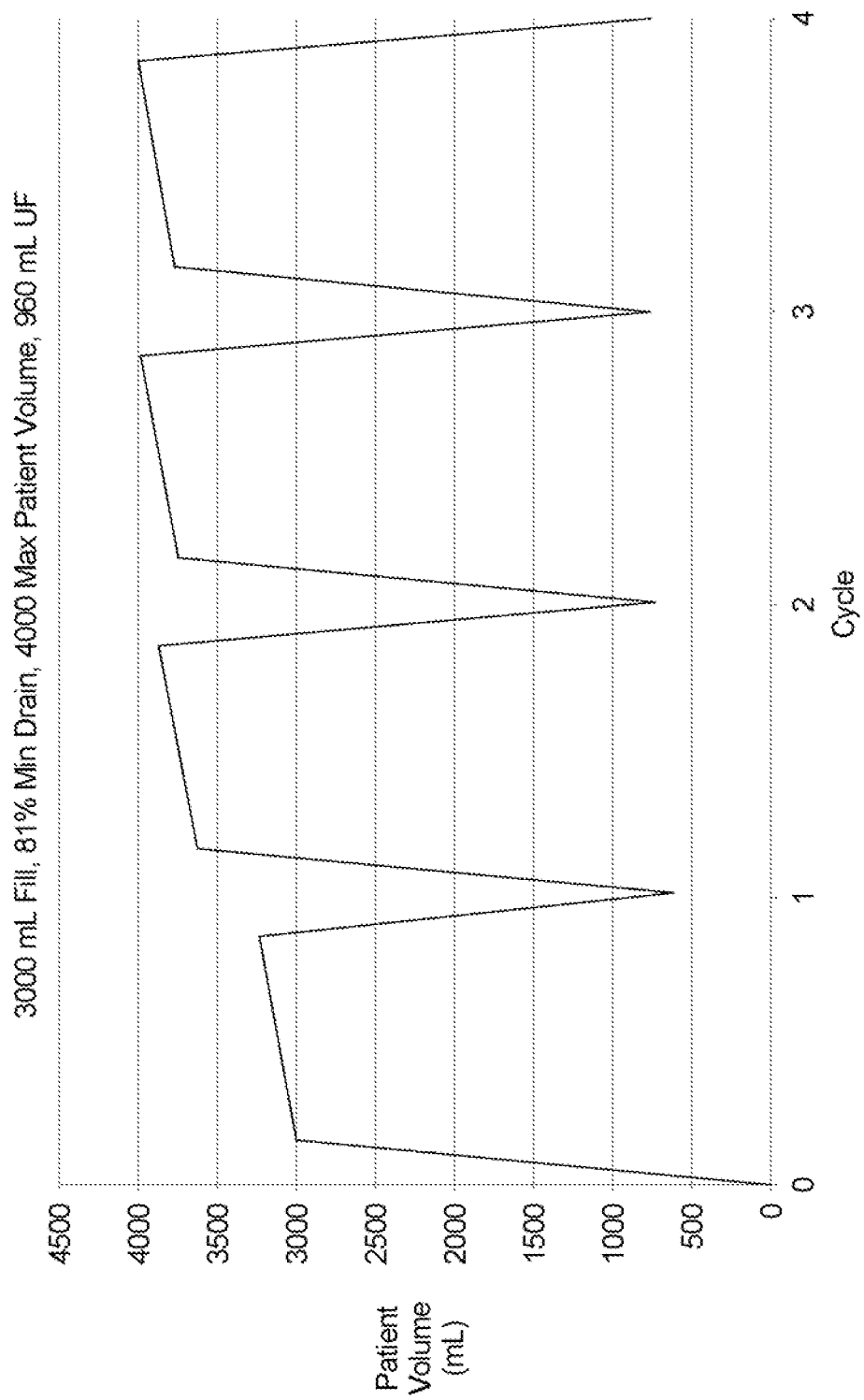
FIGS. 5 to 7 are therapy graphs illustrating another method or algorithm of the present disclosure.
Figure 6:
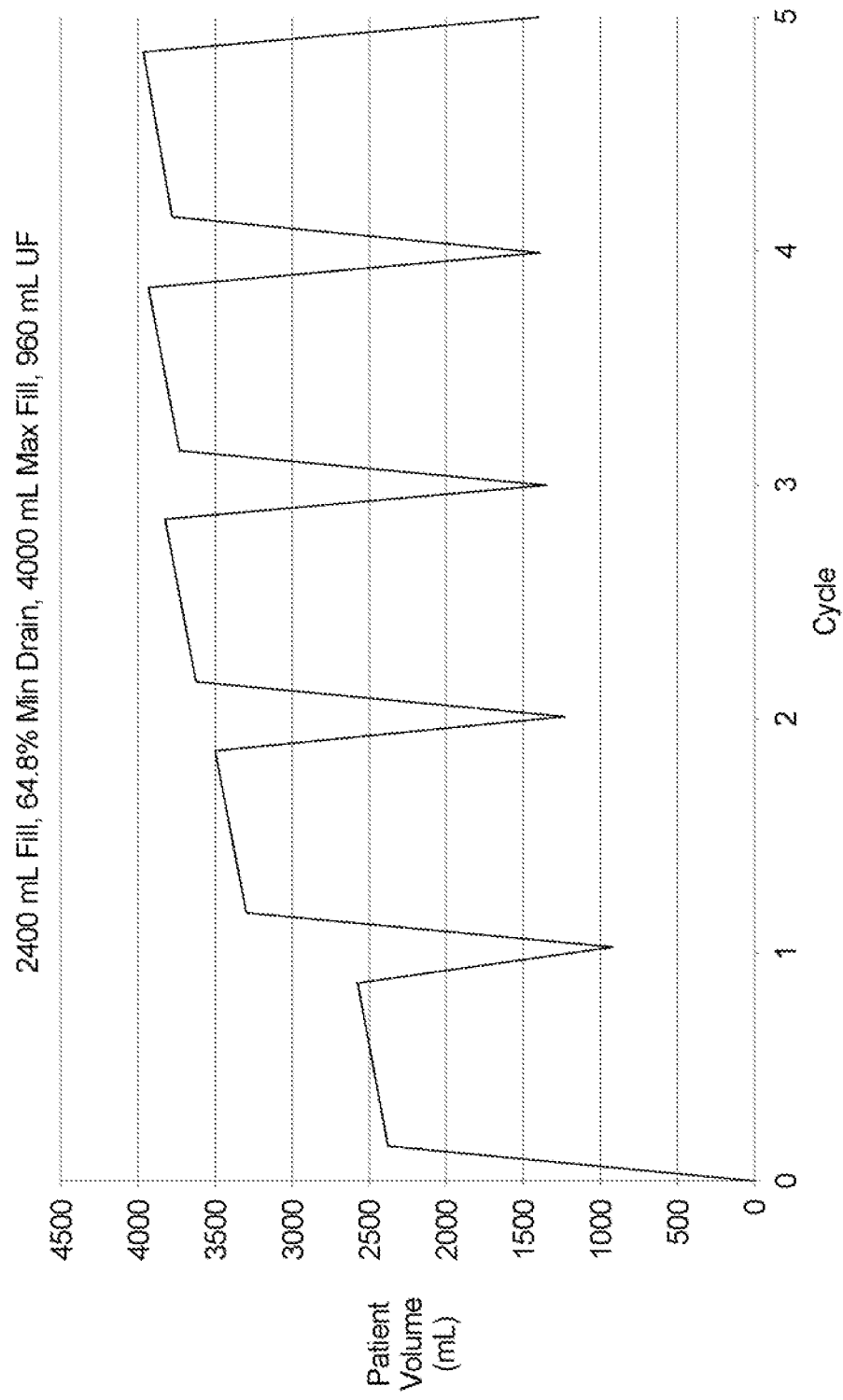

In an alternative embodiment shown in FIGS. 4 to 6, the initial minimum drain volume/percentage is calculated using a formula that is used throughout treatment whenever the minimum drain/volume percentage needs to be adjusted.

Block 104 also shows that a threshold minimum drain volume or percentage can optionally be set in one embodiment. System 10 and method 100 also understand that the patient may shift during sleep, such that the patient fill/drain line 38d (from cassette 50 to the patient) becomes partially or fully occluded. Or, drain tube 38b (from cassette 50 to drain) can become partially or fully occluded. Both situations can severely restrict the effectiveness of the drain phase, and machine 12 should wake the patient in such instances to clear the occlusion. The threshold minimum drain volume may be set to be equal to or less than 50% of the combined fill and expected UF volumes.

It is contemplated at block 104 to set the threshold minimum drain volume or percentage at the factory and update it rarely or never. In an alternative embodiment, line occlusions are determined on a more instantaneous basis, e.g., by sensing pressure spikes, such that the setting of the threshold minimum drain volume or percentage is done as an extra line occlusion (or other major error situation) check or is eliminated altogether.

System 10 and method 100 are not limited to any particular type of therapy setup. A total combined fill volume, or total volume of fresh dialysate delivered to the patient over each of the cycles, is generally set by prescription, e.g., the be twelve or eighteen liters. The durations of time needed to fill and drain the patient, that is, the time durations of the fill and drain phases, are a function of the pumping capability of machine 12 and the amount needed to be filled and drained, each of which are typically known and set. Three interrelated variables remain, namely, total number of cycles, dwell phase duration per cycle, and total therapy time or duration. Total therapy time or duration may or may not include the time needed to initially drain the patient of the previous therapy's last fill or the time needed to perform a last fill after the cycles have been completed. Regardless, setting any two of (i) the total number of cycles, (ii) dwell phase duration per cycle, and (iii) total therapy time or duration generally sets the third variable. In the illustrated embodiment, at block 104 the nurse, doctor, clinician or patient sets the total therapy time and an initial number of cycles. Dwell duration per cycle is then calculated knowing total therapy time and an initial number of cycles. System 10 and method 100 can operate alternatively setting: (i) dwell duration and number of cycles, meaning total therapy time is a dependent variable; or (ii) dwell duration and total therapy time, such that the initial number of cycles is a dependent variable.

The patient at block 104 typically enters one of the two-of-three combinations discussed above for number of cycles, dwell phase duration and total therapy time, which allows the current day's therapy to be tweaked if needed. However, system 10 and method 100 are applicable even if the two-of-three combination is preset, e.g., from a remote computer or via a prescription loaded from a clinician or doctor onto a memory device read by APD machine 12.

As seen at block 106, method 100 performs any needed precycle drain, so that therapy begins with the patient at or near empty. The initial drain is typically of a spent last fill after the previous day's exchange or from of a spent midday exchange. The initial drain is typically performed while the patient is still awake, so that the patient can move around to drain as completely as possible.

At block 108, method 100 performs a therapy cycle including a fill phase, a dwell phase and a drain phase. In the illustrated embodiment, the initial number of cycles and total therapy time are set at block 104, so that each dwell phase has a duration equal to the total therapy time less the filling and drain times divided by the number of cycles.

At diamond 110, method 100 determines if another cycle exists. In one embodiment, regardless of the outcome of the final drain phase, normal therapy is ended. Therapy has either been completed satisfactorily up to the final cycle or rectified via method 100. Also, the patient will have received all of the prescribed fresh dialysate by the time of the final drain. Still further, the patient can be awakened at the end for the final drain and can maneuver to rid himself/herself of the residual effluent volume. If a last fill (carried by the patient into the day) is to occur before the patient is awakened, it is contemplated that system 10 and method 100 append the last fill volume so as not to allow the patient to become overfilled, taking into account expected UF from the last fill. If another cycle exists, as determined at diamond 112, method 100 moves to the minimum drain comparison of diamond 112.

At diamond 112, method 100 determines if the previous drain has met the current minimum drain volume or percentage. For the first cycle, method 100 compares the initial minimum drain volume (e.g., 85% multiplied by the sum of the fill volume and the expected UF) to the actual volume drained at the end of the first cycle. If the actual volume drained does not meet the initial minimum drain volume, method 100 at diamond 114 determines whether the actual volume drained at least meets the threshold minimum drain volume, e.g., set at less than 50% multiplied by the sum of the fill volume and the expected UF. As discussed above, line occlusions may be determined using the threshold minimum drain volume and/or a different method, e.g., detecting a pressure spike. Thus, threshold minimum drain volume determination at diamond 114 can thus be eliminated if desired or kept as an additional check.

If at least the threshold minimum drain volume is met, method 100 at block 116 adds a cycle to the initial number of cycles entered at block 104. Method 100 also determines a new fill volume per cycle by dividing the total remaining volume of fresh dialysate to deliver to the patient over the previously n remaining cycles by (n+1) cycles. For example, if after the first cycle, the minimum drain is not met at diamond 112 and four fill phases remain initially at 2,500 milliliters per fill (leading to a total prescribed fill volume of five×2,500=12,500 ml), the added cycle brings the new total number of fill phases remaining to five (total cycles being six) and lowers the per fill phase volume to 10,000/5 or 2,000 milliliters per fill. Further, because the fill volume per cycle is lowered, the expected UF per cycle, which is a function of fill volume, is also lowered at block 116 of method 100. For example, if expected UF is eight percent of the fill volume, then the expected UF falls in the above example from 200 milliliters to 160 milliliters.

Method 100 at step 116 also calculates a new minimum drain volume or percentage according to the formula:

$$\text{Minimum Drain Percentage} = \frac{\text{New Fill Volume/Cycle} + \text{New } UF/\text{Cycle}}{\text{Maximum Allowable Peritoneal Volume}} \times 100\%$$

Alternatively, $$\text{Minimum Drain Threshold} =$$
$$\text{Maximum Allowable Peritoneal Volume} - (\text{Fill Volume} + UF/\text{Cycle})$$

If, for example, maximum instantaneous peritoneal volume has been set to 3000 milliliters, the new minimum drain percentage for the now remaining five cycles is (2000+2000× 0.08)/3000×100% or 72%. 72% applied to the new fill volume per cycle and new UF per cycle in the example yields 72%×2160 milliliters or 1,555 milliliters. The above equation can also be used to set the initial minimum drain volume/percentage using the initial fill volume per cycle and the initial expected UF per cycle.

Method 100 then returns to the minimum drain percentage comparison of diamond 112, now using the new minimum drain percentage and the new minimum drain volume applied retrospectively to the previous actual drain volume to see if the previous actual drain volume now meets the updated minimum drain percentage or minimum drain volume. If not, for example, if the initial, previous actual drain volume had been only 1,500 milliliters, thus not meeting the 1,555 milliliters, but still been above the threshold minimum drain volume (which assumingly is set at 50%, yielding in the example, (2,500+(2500×0.08))×0.5=1,350 milliliters), then method 100 returns to block 116 and performs its function again, adding a second additional cycle and further reducing the fill volume per cycle and expected UF per cycle, leading to an even lower new minimum drain percentage/volume. The loop between diamond 112, diamond 114 and block 116 continues until the actual drain volume meets an adjusted minimum drain percentage/volume.

As further illustrated in block 116, if the total treatment time is set as a parameter to hold constant, for example, if the patient wants to get off the machine by 7:00 AM regardless of what has occurred during the night regarding treatment, then the dwell phase duration is reduced each time a cycle is added. The formula for reducing the dwell phase duration is somewhat complicated because adding a cycle causes additional fill phase and dwell phase duration for the added cycle, which cuts into the available time for dwell. For example, if the initial prescribed therapy has 390 minutes of total dwell available, then each of the five prescribed dwells would last seventy-eight minutes assuming APD machine 12 has been set for each dwell phase to have the same duration. If a cycle is added at block 116, the new dwell period would not simply be 390 minutes divided now by six or sixty-five minutes, instead the additional fill phase and drain phase duration is subtracted first from 390 minutes, which less the seventy-eight minutes consumed over the first dwell is then divided by the new remaining number of dwells. For example, if the additional fill phase and drain phase each consume eleven minutes, the total remaining dwell time (390−78=312 minutes) is reduced by twenty-two minutes to 290 minutes and then divided by five for the remaining dwell phases, yielding fifty-eight minutes for each remaining dwell. The above recalculating of dwell duration holds total therapy time constant. Again, system 10 and method 100 do not require that total therapy time be held constant. Instead, an additional one-hundred minutes could be added to the total therapy time ((eleven for fill)+ (seventy-eight for dwell)+(eleven for fill)) or some lesser amount as desired.

Assuming in the example above that the previous actual drain volume is 2,000 milliliters, then the new minimum drain percentage/volume of 1,555 milliliters is met upon returning from block 116 to the minimum drain percentage/volume comparison at diamond 112. In this case, and in the case in which the threshold minimum drain volume is not met at diamond 114, resulting in machine 12 waking the patient and posting an alarm to clear a line occlusion or other therapy obstruction as illustrated at block 118, method 100 proceeds to perform the next therapy cycle at block 108. Up until the last cycle, any preceding drain phase not meeting the minimum drain volume/percentage is rectified in the manner described above, which can occur after multiple drain phases if needed.

When no additional cycles remain at diamond 110, method 100 of system 10 ends, as illustrated at oval 120.

Referring now to FIG. 4, method 150 illustrates an alternative CCPD embodiment, which again initially attempts to completely drain the patient at the end of each cycle. The basic difference is that with prior method 100 if the minimum drain volume/percentage at diamond 112 is not met, machine 12 undertakes the corrective measures at block 116 automatically (assuming the threshold minimum drain volume/percentage is met at diamond 114). With method 150 on the other hand, if the minimum drain volume/percentage is not met at diamond 112, the patient is instead provided with an option to take the corrective measures provided at block 116.

Method 150 begins with each of the steps and alternative implementations for oval 102, block 104, block 106 and block 108 described above with respect to method 100 of FIG. 3. Block 108 is illustrated in FIG. 4 as being split into blocks 108a and 108b, indicating that the functions of block 108a, including all alternatives discussed above at block 108 for method 100 of FIG. 3, are repeated again at block 108b. With method 150, the last cycle determination at diamond 110 is not provided directly after block 108a. Instead, at diamond 112a, method 150 determines in a first instance (including all alternatives discussed above for diamond 112 of method 100) whether the patient's actual drain has met the initial minimum drain volume/percentage. If so, method 150 then determines in a first instance if the last regular therapy cycle has just occurred at diamond 110a. If so, method 150 ends as seen at oval 120. If another cycle exists at diamond 110a, then method 150 returns system 10 to block 108a to perform another fill, dwell and drain cycle.

If the minimum drain percentage is not met at diamond 112a, then at block 124, the patient is awakened and instructed to attempt to complete the incomplete drain, e.g., to sit up and/or move the patient's stomach area in an attempt to move the indwelling catheter and/or to free one or more pocketed volume of fluid residing within the patient's peritoneal cavity. Method 150 thus provides the patient with an option to attempt to fix a minimum drain volume/percentage failure as opposed to automatically adjusting the fill volume, expected UF, and minimum drain volume/percentage accordingly as is done with method 100 of FIG. 3.

At diamond 110b, method 150 determines in a second instance whether the previous cycle was the last cycle. If so, method 150 ends again as seen at oval 120. If another cycle exists as determined at diamond 110b, method 150 at diamond 126 determines whether the patient wishes system 10 to enter into a mode in which the minimum drain volume/percentage is adjusted in a manner discussed above. APD machine 12 can make such prompt to the patient via video monitor 20, speakers 24, and/or otherwise via its user interface. The patient makes a selection to, or not to, enter the adjust minimum drain volume/percentage mode via one or more input device 22 (e.g., touch screen) in communication with the user interface and CPU of APD machine 12.

If the patient does not wish to enter the adjust minimum drain volume/percentage mode as determined at diamond 126, then method 150 returns to block 108a to perform another fill, dwell and drain cycle. Method 150 allows the patient to be awakened at block 124 each time a low drain condition occurs at diamond 112a if that is the patient's desire. If the patient experiences low drains fairly infrequently, if the cause of the low drain is usually due to a condition that the patient can typically rectify, then the patient can choose to be allowed to attempt, for each cycle, to complete a drain before advancing to the next cycle.

On the other hand, if the patient at diamond 126 feels that he/she has not effectively cleared the low drain issue experienced at block 124, is going to continue to have drain problems, wants in any case to be allowed to sleep if at all possible, or for any other reason or combination of reasons, the patient can elect to enter the adjust minimum drain mode at diamond 126. The patient can elect to enter such mode after any drain prior to the last cycle in the illustrated embodiment. Upon entering the adjust minimum drain mode, method 150 performs the remainder of the peritoneal dialysis therapy according to block 108b, diamond 110c, diamond 112b, diamond 114, diamond 116 and block 118 in the same manner as described above (including all disclosed alternatives) at block 108, diamond 110, diamond 112, diamond 114, block 116 and block 118 for method 100 of FIG. 3.

Figure 7:
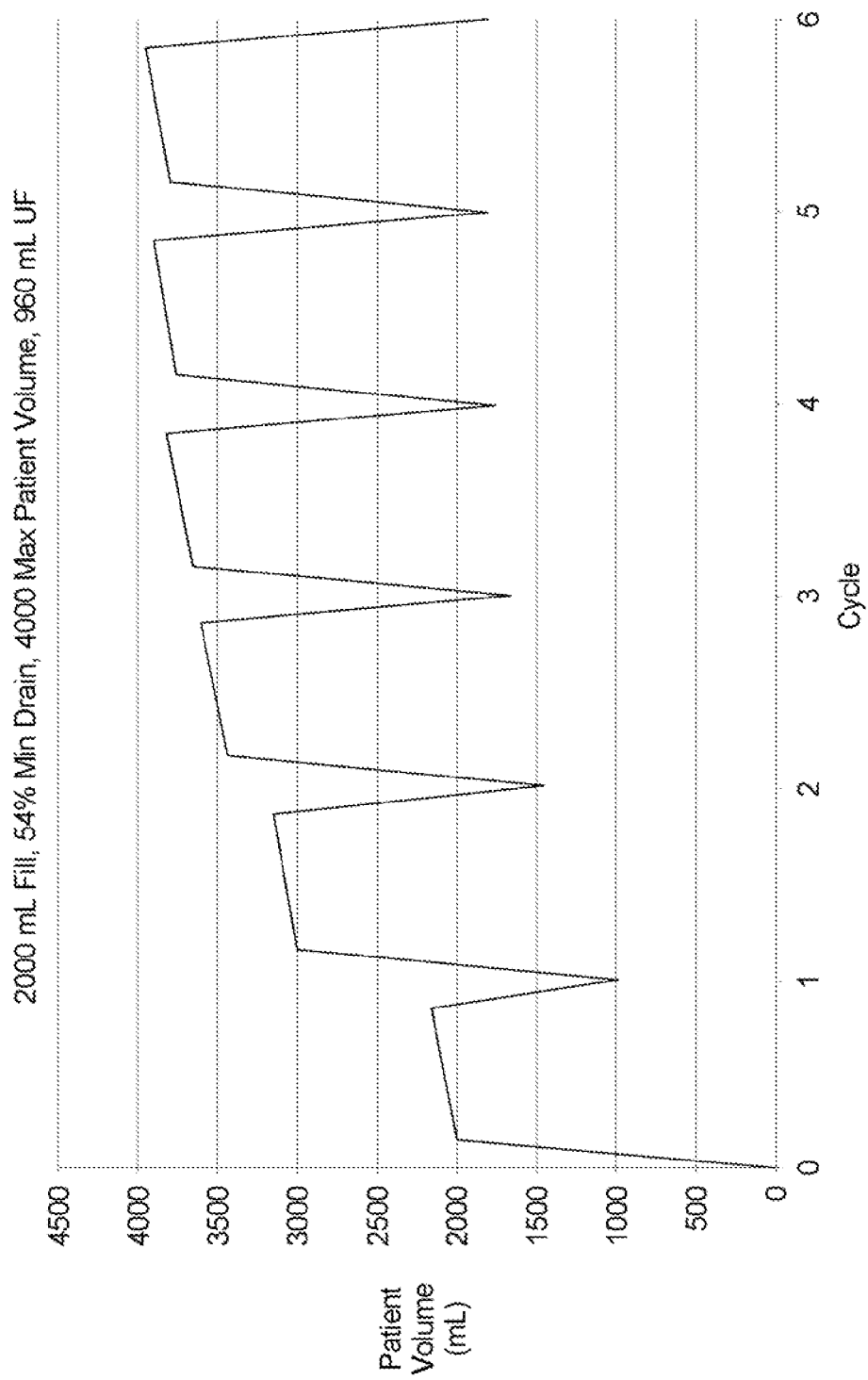

In a further alternative embodiment, illustrated in FIGS. 5 to 7, when an actual drain does not meet the minimum drain percentage/volume, the per cycle fill volume is not lowered to a value based on how much total fresh fluid remains to be delivered to the patient, as is the case with methods 100 and 150, but is instead lowered to a value based on a new average amount over the new number of cycles. FIG. 5 illustrates an initially prescribed therapy in which the initial fill phase volume per cycle is 3000 milliliters, there are four cycles yielding 12,000 milliliters of fresh overall, the maximum allowable instantaneous peritoneal volume is 4000 milliliters, expected UF is 8% or 240 milliliters per cycle, and initial minimum drain volume percentage is, here, calculated using the formula:

$$\text{Minimum Drain Percentage} = \frac{\text{Fill Volume/Cycle} + UF/\text{Cycle}}{\text{Maximum Allowable Peritoneal Volume}} \times 100\%$$

to be (3000+240)/4000×100%=81%.

Alternatively, a minimum drain threshold is calculated and used instead of the minimum drain percentage:

$$\text{Minimum Drain Threshold} = \text{Maximum Allowable Peritoneal Volume} - (\text{Fill Volume} + UF/\text{Cycle})$$

is calculated to be 4000−(3000+240)=760 milliliters. This alternative minimum drain volume establishes the maximum residual volume that can remain in the patient's peritoneal cavity prior to proceeding to the next fill.

Minimum drain percentage is different than minimum drain threshold. Minimum drain percentage is multiplied by the estimated patient volume at the end of the dwell giving a volume that is the minimum drain volume equal to the minimum amount of fluid that needs to be drained before the next fill can occur. For minimum drain threshold, the estimated patient volume at the end of dwell is reduced to a volume that is less than the minimum drain threshold. Thus if for example the estimated patient volume at the end of a particular dwell is equal to 3,999 milliliters and the minimum drain threshold is seven-hundred sixty milliliters, then the cycler should drain more than 3999−760=3,239 milliliters. At the end of the drain then, the expected patient volume should be no more than 760 mL, which is the situation at the end of cycle three in FIG. 5. The two equations yield essentially the same results at the end of the dwell of cycle 3, wherein the estimated patient volume=3,999 milliliters. Minimum drain volume of the first equation=3,999 milliliters*81%=3,239 milliliters, which allows for 760 milliliters off effluent to remain in the patient.

The difference in the two equations is that for the first minimum drain percentage equation, the allowable residual volume is less on the first cycle and it grows asymptotically. The second minimum drain threshold equation yields the residual volume and that volume is the same for every cycle. Another way of saying this is that the residual volume of the minimum drain threshold equation is the asymptote that the first minimum drain percentage equation approaches. So by the time of the last cycle, the two equations provide essentially the same result. On the first cycle, the first minimum drain percentage equation requires more volume to be drained. However, with either equation, maximum patient volume is not allowed to be exceeded.

FIG. 5 shows the worst case peritoneal volume scenario for the 81% minimum drain volume therapy. That is, each actual drain just meets the 81% minimum drain volume. As illustrated, the maximum instantaneous peritoneal volume nonetheless never exceeds the programmed limit of 4000 ml.

If the residual volume at the end of any but the last drain is insufficient, that is, does not meet the 81% minimum drain, the therapy is modified to use the same total fluid volume of 12,000 milliliters over five cycles instead of four. The fill volume per cycle in the example of FIG. 5 is decreased to, on average, 2400 ml. The per cycle UF falls from 240 ml to 192 ml.

In method 100, suppose the first two cycles are performed as prescribed consuming 6000 milliliters, leaving 6000 milliliters for the original final two cycles. The third cycle results in an insufficient drain, so a fifth cycle is added. Method 100 at FIG. 3 teaches dividing the remaining 6000 milliliters by the three remaining cycles, yielding 2000 milliliters per cycle. The example of FIG. 5 instead uses the average value of 2400 ml instead. In the example of FIG. 5, then the final fill volume assuming therapy continues after adding just the single cycle is shorted to only be 1,200 milliliters, the remaining amount of fresh solution.

In the alternative method of FIG. 5, when a first cycle is added as illustrated in FIG. 6, using the new average fill volume per cycle and the new average UF per cycle, a new minimum drain percentage is calculated using the formula:

$$\text{Minimum Drain Percentage} = \frac{\text{New Ave. Fill Volume/Cycle} + \text{New Ave. }UF/\text{Cycle}}{\text{Maximum Allowable Peritoneal Volume}} \times 100\%$$

Is calculated to be (2400+192)/4000×100%=64.8%.

FIG. 6 shows the worst case peritoneal volume scenario for the 64.8% minimum drain volume therapy. That is, each actual drain just meets the 64.8% minimum drain volume. As illustrated, the maximum peritoneal volume nonetheless never exceeds the programmed limit of 4000 ml.

If the residual volume at the end of drain is still insufficient even after adding a cycle using the alternative embodiment of FIGS. 5 to 7, therapy is modified to use the same total fresh fluid volume of 12000 ml over six cycles instead of five. The average fill volume decreases to 2000 milliliters per cycle. The average per cycle UF falls from 192 ml to 160 ml.

The new minimum drain percentage is calculated again using the formula:

$$\text{Minimum Drain Percentage} = \frac{\text{New Ave. Fill Volume/Cycle} + \text{New Ave. }UF/\text{Cycle}}{\text{Maximum Allowable Peritoneal Volume}} \times 100\%$$

Is calculated to be (2000+160)/4000×100%=54%.

FIG. 7 illustrates the worst case peritoneal volume scenario for the 54% minimum drain volume therapy using the method of the invention. That is, each actual drain just meets the 54% minimum drain volume. The maximum peritoneal volume nonetheless never exceeds the programmed limit of 4000 milliliters.

In FIGS. 5 to 7, the maximum residual peritoneal volume at the end of drain increases from (i) 760 milliliters for the 81% minimum drain with 3000 milliliters nominal fill volume to (ii) 1,408 milliliters for the 64.8% minimum drain volume with 2400 milliliters nominal fill, to (iii) 1840 milliliters for the 54% minimum drain with 2000 milliliters nominal fill volume. The maximum allowable instantaneous peritoneal volume in all three cases is the same, namely, 4000 milliliters. The methodology of FIGS. 5 to 7 can be implemented automatically, as with method 100, or be implemented by patient preference, as with method 150.

In the embodiment of FIGS. 5 to 7, the relationship between the maximum allowable instantaneous peritoneal volume, the nominal or average fill volume per cycle, the per cycle UF and the minimum drain volume/percentage can be characterized by the equations below, which provide proof that the peritoneal volume at the end of dwell for the alternative embodiment of FIGS. 5 to 7 never exceeds the maximum peritoneal volume.

The minimum drain volume is a function of the fill volume, the cycle UF and the residual volume remaining in the patient's peritoneum at the end of each drain. The minimum drain percentage is (fill volume+cycle UF)/maximum peritoneal volume for the alternative embodiment of FIGS. 5 to 7. The minimum drain volume for each cycle=minimum drain percentage*(fill volume+the cycle UF+previous drain residual volume). The proof is as follows:

Patent Volume at End of Dwell 1 = Fill Volume + Cycle $UF$    (i)

Residual Volume at end of Drain 1 =    (ii)
(Fill Volume + Cycle $UF$) * (1 − Min Drain %) if drain ended when exactly the minimum volume had been drained.

Patent Volume at End of Dwell 2 =    (iii)
Fill Volume + Cycle $UF$ + Residual Volume at End of Drain 1

Residual Volume at end of Drain 2 =    (iv)
Patent Volume at End of Dwell 2 * (1 − Min Drain %) if drain ended when exactly the minimum volume had been drained Patent Volume at End of Dwell 3 =    (v)
Fill Volume + Cycle $UF$ + Residual Volume at End of Drain 2

Patent Volume at End of Dwell 3 =    (vi)
(Fill Volume + Cycle $UF$) * [(1 − Min Drain %)$^0$ + (1 − Min Drain %)$^1$ + (1 − Min Drain %)$^2$)]

Patent Volume at End of Dwell 3 =    (vii)

$$(\text{Fill Volume} + \text{Cycle }UF) * \sum_{J=0}^{2} (1 - \text{Min Drain \%})^J$$

Eqn 1

Patent Volume at End of Dwell $N$ =    (viii)

$$(\text{Fill Volume} + \text{Cycle }UF) * \sum_{J=0}^{N-1} (1 - \text{Min Drain \%})^J$$

Multiply each side of the equal for Patent Volume    (ix)
at End of Dwell $N$ by (1 − Min Drain %) and obtain Eqn 2

(1 − Min Drain %) * Patent Volume at End of Dwell $N$ =    (x)

$$(\text{Fill Volume} + \text{Cycle }UF) * \sum_{J=1}^{N} (1 - \text{Min Drain \%})^J$$

Subtract Equation 2 from equation 1 and obtain    (xi)
Min Drain % * Patent Volume at End of Dwell $N$ =
(Fill Volume + Cycle $UF$) * (1 − Min Drain %)$^0$ + (1 − Min Drain %)$^N$ $$\text{Min Drain \%} = \frac{(1 - \text{Min Drain \%})^0 + (1 - \text{Min Drain \%})^N}{\text{Patent Volume at End of Dwell }N} *$$    (xii)

(Fill Volume + Cycle $UF$) and

Patent Volume at End of Dwell $N$ =    (xiii)

$$\frac{(1 - \text{Min Drain \%})^0 + (1 - \text{Min Drain \%})^N}{\text{Min Drain \%}} *$$

(Fill Volume + Cycle $UF$)

Since 1 = (1 − Min Drain %)$^0$ and as $N$ becomes very large,    (xiv)
(1 − Min Drain %)$^N$ will become equal zero because
(1 − Min Drain %) < 1 these two equations reduce to Eqn 3

$$\text{Min Drain \%} = \frac{(\text{Fill Volume} + \text{Cycle }UF)}{\text{Patent Volume at End of Dwell }N} \text{ and}$$    (xv)

Eqn 4

$$\text{Patent Volume at End of Dwell }N = \frac{(\text{Fill Volume} + \text{Cycle }UF)}{\text{Min Drain \%}}$$    (xvi)

As seen in the above proof for the alternative embodiment of FIGS. 5 to 7, because the minimum drain %=(fill volume+ cycle UF)/maximum peritoneal volume, substituting minimum drain % in Eqn 4, it follows that patient volume at end of dwell n=maximum peritoneal volume.

A further alternative method for a controlling minimum drain volume is to establish the maximum residual volume that can remain in the patient's peritoneal cavity prior to proceeding to the next fill. This volume is given by: maximum residual volume=maximum peritoneal volume ("MPV")−(fill volume+cycle UF). In this further alternative method, the estimated peritoneal volume at the end of each drain phase is compared to the maximum residual volume, and if the estimated peritoneal volume is less than the maximum residual volume, the next fill can proceed without exceeding the MPV. The estimated peritoneal volume at the end of each drain for this further alternative method=(Σfill volumes (1 to N)+Σcycle UF (1 to N))−Σdrain volumes (1 to N)

2. Tidal Therapies

Referring now to FIGS. 8 to 10, embodiments for tidal therapies are illustrated. In one implementation, when the patient, clinician or doctor elects that the patient run a tidal therapy, machine 12 of system 10 queries, e.g., via video monitor 20 and/or voice guidance via speakers 24, whether the patient wishes to run a "plus one" tidal therapy or a "plus two" tidal therapy. FIG. 8 illustrates a baseline CCPD therapy used to calculate the "plus one" tidal therapy of FIG. 9 and the "plus two" tidal therapy of FIG. 10.

The tidal therapy of the present disclosure can be entered as a CCPD therapy, which is generally easier to do. Indeed, it is contemplated to begin with a stored CCPD therapy that could be performed alternatively as a CCPD therapy if selected at the CCPD versus tidal therapy screen on video monitor 20. But once a suitable CCPD therapy is selected to be run instead as a tidal therapy, machine 12 of system 10 prompts the patient, clinician or caregiver to select either "plus one" or "plus two", indicating that one additional cycle is to be added to the selected CCPD therapy or that two additional cycles are added to be added to the selected CCPD therapy. In one embodiment, regardless of whether the "plus one" or the "plus two" tidal therapy is chosen: (i) the total treatment time is held constant with that of the selected CCPD therapy, (ii) the same total volume of fresh dialysate prescribed for the CCPD therapy is delivered to the patient over the course of the fill phases, (iii) the patient is filled to the same volume after each fill as is done with the selected CCPD therapy, and (iv) total therapy duration is held constant with that of the selected CCPD therapy.

FIG. 8 illustrates the CCPD therapy that the patient, clinician or doctor has selected for modification into a tidal therapy, and which is displayed on display device 20 of machine 12 of system 10. If the patient runs the CCPD therapy of FIG. 8 instead of a tidal therapy, the previous day's, last fill or midday fill takes approximately thirty minutes to drain completely. Then, four cycles are performed in which the patient is filled in each case to 2,500 milliliters, thus using 10,000 milliliters over the entire total therapy. Each cycle, including fill, dwell and complete drain phases, lasts about two hours and fifteen minutes (135 minutes) leading to a total therapy time of about nine hours (540 minutes). With expected UF (e.g., eight percent of fill volume) removed over each dwell cycle, the patient's maximum instantaneous intraperitoneal volume is about 2,700 milliliters at the end of each dwell phase. At the end of the drain phase for the fourth cycle, the patient is given a final fill for the day (or until a midday exchange is performed) of 2,000 milliliters.

In one embodiment, the patient, clinician or doctor can choose between adding one or two additional cycles to the selected CCPD therapy. FIG. 9 illustrates an example of when a single cycle has been added. As illustrated, system 10 converts the CCPD cycle of FIG. 8 to the tidal therapy of FIG. 9, which shortens each of the first, second, third and fourth drains to leave a twenty-five percent residual volume for each of the second, third, fourth and fifth cycles. The fifth drain phase drains the patient completely. Machine 12 in one embodiment wakes the patient for the fifth or final drain phase, or at the end of the fifth and final drain phase, so that the patient can move around, sit up, or perform whatever maneuver helps the patient to drain completely.

A typical drain phase curve for a patient shows a linear change in volume, similar to the linear downwardly extending lines of the drain phases illustrated in FIGS. 8 to 10. At a certain transition point in the drain, the volume profile becomes non-linear and slows appreciably, forming a downwardly sloping parabolic curve that asymptotically approaches a full drain. This phenomenon is shown and described in detail in copending U.S. patent application Ser. No. 12/389,886, now U.S. Pat. No. 8,521,482, entitled, "Simulation of Patent Drain Phase in Peritoneal Dialysis", filed Feb. 20, 2009, the entire contents of which are incorporated herein by reference and relied upon.

For the tidal therapy of FIG. 9, it is hoped that a prescribed twenty-five percent residual volume of fluid that is allowed to remain in the patient's peritoneum, meaning that patient drains seventy-five percent of the fill volume (including either just fresh dialysate, or fresh dialysate plus previous residual drain), will result in the drain stopping before the patient transitions from the efficient linear drain to the less effective parabolic drain. It is therefore attempted that the drain of FIG. 9 be performed efficiently all the way through to the twenty-five percent residual volume.

If the patient finds that he/she cannot meet the twenty-five percent residual drain volume on a consistent enough basis, e.g., the patient transitions to the less efficient non-linear drain before draining seventy-five percent of the fill volume, the patient, clinician or doctor can instead elect the selected CCPD therapy plus two additional cycles shown in FIG. 10. The "plus two" cycle therapy sets the patient's residual drain volume to be forty percent of the fill volume (including either just fresh dialysate, or fresh dialysate plus previous residual drain). In either the "plus one" or "plus two" tidal therapy, system 10 advantageously allows the tidal therapy to be automatically set into memory from the selected CCPD therapy as opposed to requiring the patient, clinician or doctor to enter all the specifics of the tidal therapy.

In FIG. 9, after the initial drain of the last fill or midday exchange of the previous therapy, which takes again about thirty minutes, the first fill is a complete fill to 2,500 milliliters set by the chosen CCPD therapy. Because one additional cycle is added to the therapy of FIG. 9, totaling five, each cycle is lessened in duration to one-hundred and eight minutes, resulting in the same total therapy time of nine hours (540 minutes) as the selected CCPD therapy.

The drain phase for each of the first, second, third and fourth cycles is shortened to leave 625 milliliters in the patient's peritoneal cavity (25% of the 2,500 milliliter initial fill and total volume at the end of each subsequent fill). Each of the second, third, fourth and fifth fills is then shortened to 1,875 milliliters, resulting in the same initial intraperitoneal fill volume of 2,500 milliliters, which is consistent with each of the fills of the selected CCPD therapy of FIG. 8. A total therapy volume of 10,000 milliliters (2,500+4×1,875) is delivered to the patient over the five cycles, which is also the same as the total amount fresh fluid delivered to the patient in the selected CCPD therapy.

In FIG. 10, after the initial drain of the last fill or midday exchange of the previous therapy, which takes again about thirty minutes, the first fill is a complete fill to 2,500 milliliters set by the chosen CCPD therapy. Because two additional cycles are now added to the therapy of FIG. 10, totaling six, each cycle is lessened in duration to ninety minutes, resulting in the same total therapy time of nine hours (540 minutes) as the selected CCPD therapy.

The drain phase for each of the first, second, third, fourth and fifth cycles is shortened to leave 1000 milliliters in the patient's peritoneal cavity (40% of the 2,500 milliliter initial fill and total volume at the end of each subsequent fill). Each of the second, third, fourth, fifth and sixth fills is then shortened to 1,500 milliliters, resulting in the same initial intraperitoneal fill volume of 2,500 milliliters, which is consistent with each of the fills of the selected CCPD therapy of FIG. 8. A total therapy volume of 10,000 milliliters (2,500+5×1,500) is delivered to the patient over the six cycles, which is also the same as the total amount fresh fluid delivered to the patient in the selected CCPD therapy of FIG. 8.

The tidal therapy methodology of the present disclosure is not limited to the "plus one" or "plus two" regimes discussed herein. Three or more cycles can be added instead.

In typical CCPD methods, care should be taken to ensure that large amounts of unused solution do not result. To calculate an initial number of night cycles that will consume all the fluid, it is contemplated to use an 85% rule. Here, the number of CCPD cycles=total night therapy volume/night fill volume per cycle. If the result does not divide evenly, the remainder is examined and if the remainder is >0.85, the therapy is rounded-up to the next number of cycles, if the remainder is <0.85, the number of cycles is truncated.

In an example, if the total night therapy volume=10,000 milliliters, and the desired fill volume per cycle is 2,500 milliliters, then 10,000/2500=four cycles with zero remainder and thus no solution was wasted. If the desired fill volume per cycle is instead 2600 milliliters rather than 2500, the same algorithm results in 10,000/2600=3.846, and since 0.846<0.85, the result is truncated to three cycles. Total night therapy volume actually used is then 2600 milliliters×three cycles=7,800 milliliters and 2,200 milliliters of the desired 10,000 milliliters is not used.

But the 2600 milliliter therapy could be converted to a tidal therapy per FIGS. 8 to 10 with the result that all solution would be used. For a plus one therapy, for example, there would be a total of four cycles. 10,000 milliliters−2600 milliliters (initial full fill)=7400 milliliters/three remaining cycles=2467 milliliters over the three remaining cycles results in a tidal percentage of 98% and a patient residual volume of only 33 milliliters, which would not be an optimal therapy due to the high tidal percentage. A plus two tidal therapy according to FIGS. 8 to 10 would be more optimal, resulting in 7400 milliliters/four remaining cycles=1850 milliliters, a tidal percentage of 71% and a corresponding patient residual volume of 750 milliliters with all solution volume used.

Thus, the methodology of FIGS. 8 to 10 allows for selection from a number of optional therapies to determine an optimized therapy, taking into account, for example, a desired fill volume. The tidal therapy system and method of FIGS. 8 to 10 also enables the clinician to gradually increase the fill volume, e.g., from 2000 milliliters to 2100 milliliters to 2200 milliliters per cycle, without changing the total night therapy volume and without wasting solution.

ASPECTS OF THE PRESENT DISCLOSURE

Aspects of the subject matter described herein may be useful alone or in combination one or more other aspect described herein. Without limiting the foregoing description, in a first aspect of the present disclosure, a system for performing a peritoneal dialysis therapy includes: at least one dialysis fluid pump; and a control unit operable with the at least one dialysis fluid pump to perform a plurality of peritoneal dialysis cycles, the cycles including a fill phase, a dwell phase and a drain phase, the control unit configured to: (i) avoid a maximum peritoneal volume being exceeded after any of the dwell phases of the plurality of patient cycles, (ii) ensure that a total sum of dialysis fluid volume of the fill phases as prescribed is delivered to the patient, and (iii) if a residual volume left in the patient after one of the drain phases is determined to cause (i) to be violated during a next cycle, reduce an amount of dialysis fluid volume of the fill phase of the next cycle and add an additional cycle to the peritoneal dialysis therapy so that (ii) is satisfied.

In accordance with a second aspect of the present disclosure, which may be used in combination with the first aspect, for the first cycle, satisfying (i) includes ensuring that the prescribed fill volume plus an expected ultrafiltration volume per cycle is less than the maximum peritoneal volume.

In accordance with a third aspect of the present disclosure, which may be used in combination with any one or more of the preceding aspects, satisfying (i) includes ensuring that the fill volume plus an expected ultrafiltration volume per cycle plus a residual volume of fluid leftover from a previous drain phase is less than the maximum peritoneal volume.

In accordance with a fourth aspect of the present disclosure, which may be used in combination with the third aspect, the expected ultrafiltration volume is a percentage of the fluid volume of the fill phase as described.

In accordance with a fifth aspect of the present disclosure, which may be used in combination with any one or more of the preceding aspects, the control unit in (iii) is configured to reduce the amount of the dialysis fluid volume for each of the remaining fill phases.

In accordance with a sixth aspect of the present disclosure, which may be used in combination with any one or more of the preceding aspects, the control unit in (iii) is configured to reduce the amount of the dialysis fluid volume of each of the remaining fill phases by a same amount.

In accordance with a seventh aspect of the present disclosure, which may be used in combination with any one or more of the preceding aspects, the control unit in (iii) is configured to reduce the amount of the dialysis fluid volume for each of the remaining fill phases to an amount equal to a remaining portion of the total sum of dialysis fluid volume divided by a remaining number of cycles including the added cycle.

In accordance with an eighth aspect of the present disclosure, which may be used in combination with the seventh aspect, the control unit is further configured to change a minimum drain percentage to the reduced fill amount plus an expected ultrafiltration volume per cycle leading to an outcome that is divided by the maximum peritoneal volume.

In accordance with a ninth aspect of the present disclosure, which may be used in combination with any one or more of the preceding aspects, the control unit is configured to perform (iii) a plurality of times if needed.

In accordance with a tenth aspect of the present disclosure, which may be used in combination with any one or more of the preceding aspects, the control unit in (iii) is configured to (a) reduce the amount of the dialysis fluid volume of each of the remaining fill phases to a first amount equal to a first remaining portion of the total sum of dialysis fluid volume divided by the remaining number of cycles including a first added cycle, and if needed to (b) reduce the amount of the dialysis fluid volume of each of the remaining fill phases to a second amount equal to a second remaining portion of the total sum of dialysis fluid volume divided by the remaining number of cycles including a second added cycle.

In accordance with an eleventh aspect of the present disclosure, which may be used in combination with the tenth aspect, the control unit is further configured to (c) change a minimum drain percentage a first time in (a) to the first amount plus an expected ultrafiltration volume leading to a first outcome that is divided by the maximum peritoneal volume and (d) change the minimum drain percentage a second time in (b) to the second amount plus an expected ultrafiltration volume leading to a second outcome that is divided by the maximum peritoneal volume.

In accordance with a twelfth aspect of the present disclosure, which may be used in combination with the eleventh aspect, the expected ultrafiltration volume in (c) is different then the expected ultrafiltration volume in (d) due to the first amount being different than the second amount.

In accordance with a thirteenth aspect of the present disclosure, which may be used in combination with any one or more of the preceding aspects, the control unit is further configured to reduce a duration of the dwell phase in the next cycle.

In accordance with a fourteenth aspect of the present disclosure, which may be used in combination with any one or more of the preceding aspects, the control unit is further configured to perform (i), (ii) and (iii) upon a user election to perform a continuous cycling peritoneal dialysis therapy as opposed to a tidal dialysis therapy.

In accordance with a fifteenth aspect of the present disclosure, which may be used in combination with any one or more of the preceding aspects, the control unit is configured to perform (iii) upon a user election to modify an initially prescribed peritoneal dialysis therapy or (iii) automatically based on a preconfigured allowance.

In accordance with a sixteenth aspect of the present disclosure, which may be used in combination with any one or more of the preceding aspects, a system for performing a peritoneal dialysis therapy includes: at least one dialysis fluid pump; and a control unit operable with the at least one dialysis fluid pump to perform a plurality of peritoneal dialysis cycles, the cycles including a fill phase, a dwell phase and a drain phase, the control unit configured to: (i) ensure that a total sum of dialysis fluid volume of the fill phases as prescribed is delivered to the patient, and (ii) if a minimum drain percentage after one of the drain phases cannot be achieved, reduce an amount of dialysis fluid volume of the fill phase of the next cycle and add an additional cycle to the peritoneal dialysis therapy so that (i) is satisfied.

In accordance with a seventeenth aspect of the present disclosure, which may be used with any one or more of the preceding aspects in combination with the sixteenth aspect, the control unit in (ii) is configured to reduce the amount of the dialysis fluid volume for each of the remaining fill phases.

In accordance with an eighteenth aspect of the present disclosure, which may be used with any one or more of the preceding aspects in combination with the seventeenth aspect, the control unit in (ii) is configured to reduce the amount of the dialysis fluid volume for each of the remaining fill phases to an amount equal to a remaining portion of the total sum of dialysis fluid volume divided by a remaining number of cycles including the added cycle.

In accordance with a nineteenth aspect of the present disclosure, which may be used with any one or more of the preceding aspects in combination with the sixteenth aspect, the control unit is further configured to change a minimum drain percentage to the reduced fill amount plus an expected amount of ultrafiltration leading to an outcome that is divided by the maximum peritoneal volume.

In accordance with a twentieth aspect of the present disclosure, which may be used with any one or more of the preceding aspects in combination with the sixteenth aspect, the control unit is further configured to reduce a duration of the dwell phase in the next cycle.

In accordance with a twenty-first aspect of the present disclosure, which may be used with any one or more of the preceding aspects in combination with the sixteenth aspect, the control unit is further configured to perform (i) and (ii) upon a user election to perform a continuous cycling peritoneal dialysis therapy as opposed to a tidal dialysis therapy.

In accordance with a twenty-second aspect of the present disclosure, which may be used with any one or more of the preceding aspects in combination with the sixteenth aspect, the control unit is configured to perform (ii) upon a user election to modify an initially prescribed peritoneal dialysis therapy or to perform (ii) automatically based on a setting preconfigured by a clinician.

In accordance with a twenty-third aspect of the present disclosure, which may be used in combination with any one or more of the preceding aspects, a system for performing peritoneal dialysis includes: at least one dialysis fluid pump; and a control unit operable with the at least one dialysis fluid pump to perform a plurality of peritoneal dialysis cycles, the cycles including a fill phase, a dwell phase and a drain phase, the control unit configured to: (i) ensure that at the end of the dwell phase of each cycle, a maximum peritoneal volume is not exceeded, (ii) ensure that a total prescribed dialysis fluid volume is delivered to the patient over the fill phases of the cycles, and (iii) monitor each drain phase to ensure a minimum drain volume is met, and if not, shorten a subsequent fill phase to comply with (i) and add a cycle to comply with (ii).

In accordance with a twenty-fourth aspect of the present disclosure, which may be used with any one or more of the preceding aspects in combination with the twenty-third aspect, the system includes a total prescribed time for the cycles in aggregate, the control unit further configured to lessen a duration of at least one subsequent dwell phase if a cycle is added in (iii).

In accordance with a twenty-fifth aspect of the present disclosure, which may be used with any one or more of the preceding aspects in combination with the twenty-third aspect, the control unit is further configured to perform (i), (ii) and (iii) upon an initial user election to perform a continuous cycling peritoneal dialysis therapy as opposed to a tidal dialysis therapy.

In accordance with a twenty-sixth aspect of the present disclosure, which may be used with any one or more of the preceding aspects in combination with the twenty-third aspect, the control unit is configured to perform (iii) upon a user election to modify an initially prescribed peritoneal dialysis therapy.

In accordance with a twenty-seventh aspect of the present disclosure, which may be used with any one or more of the preceding aspects in combination with the twenty-third aspect, the minimum drain volume is the maximum peritoneal volume−(fill phase volume plus an expected ultrafiltrate volume per cycle).

In accordance with a twenty-eighth aspect of the present disclosure, which may be used in combination with any one or more of the preceding aspects, a system for performing a peritoneal dialysis therapy includes: at least one dialysis fluid pump; and a control unit operable with the at least one dialysis fluid pump to perform a plurality of peritoneal dialysis cycles, the cycles including a fill phase, a dwell phase and a drain phase, the control unit configured to: (i) store a previously entered continuous cycling peritoneal dialysis ("CCPD") therapy having a total prescribed fresh dialysate fill volume delivered over n cycles, the cycles performed over a total therapy duration; and (ii) automatically convert the CCPD therapy into a tidal peritoneal dialysis therapy having n+1 cycles, using the total prescribed fresh dialysis fill volume, and maintaining the total therapy duration.

In accordance with a twenty-ninth aspect of the present disclosure, which may be used with any one or more of the preceding aspects in combination with the twenty-eighth aspect, the control unit is configured to provide an option to perform (ii), wherein the tidal therapy is a first tidal therapy or to instead perform (iii), wherein the CCPD therapy is automatically converted to a second tidal therapy having n+2 cycles, using the total prescribed fresh dialysate fill volume, and maintaining the total therapy duration.

In accordance with a thirtieth aspect of the present disclosure, which may be used with any one or more of the preceding aspects in combination with the twenty-ninth aspect, the first tidal therapy has a prescribed first residual drain volume and the second tidal therapy has a prescribed second, higher, residual drain volume.

In accordance with a thirty-first aspect of the present disclosure, which may be used with any one or more of the preceding aspects in combination with the twenty-eighth aspect, the control unit is further configured to perform (i) and (ii) upon a user's election to perform a tidal therapy peritoneal dialysis as opposed to a CCPD dialysis therapy.

In accordance with a thirty-second aspect of the present disclosure, which may be used with any one or more of the preceding aspects in combination with the twenty-eighth aspect, the control unit is further configured such that a volume residing in a patient after each of the fills of the tidal therapy is at least substantially equal to the volume that would reside in the patient after each of the fills of the CCPD therapy.

In accordance with a thirty-third aspect of the present disclosure, any of the structure and functionality illustrated and described in connection with FIG. 1 may be used in combination with any one or more of the preceding aspects.

In accordance with a thirty-forth aspect of the present disclosure, any of the structure and functionality illustrated and described in connection with FIG. 2 may be used in combination with any one or more of the preceding aspects.

In accordance with a thirty-fifth aspect of the present disclosure, any of the structure and functionality illustrated and described in connection with FIG. 3 may be used in combination with any one or more of the preceding aspects.

In accordance with a thirty-sixth aspect of the present disclosure, any of the structure and functionality illustrated and described in connection with FIG. 4 may be used in combination with any one or more of the preceding aspects.

In accordance with a thirty-seventh aspect of the present disclosure, any of the structure and functionality illustrated and described in connection with FIG. 5 may be used in combination with any one or more of the preceding aspects.

In accordance with a thirty-eighth aspect of the present disclosure, any of the structure and functionality illustrated and described in connection with FIG. 6 may be used in combination with any one or more of the preceding aspects.

In accordance with a thirty-ninth aspect of the present disclosure, any of the structure and functionality illustrated and described in connection with FIG. 7 may be used in combination with any one or more of the preceding aspects.

In accordance with a fortieth aspect of the present disclosure, any of the structure and functionality illustrated and described in connection with FIG. 8 may be used in combination with any one or more of the preceding aspects.

In accordance with a forty-first aspect of the present disclosure, any of the structure and functionality illustrated and described in connection with FIG. 9 may be used in combination with any one or more of the preceding aspects.

In accordance with a forty-second aspect of the present disclosure, any of the structure and functionality illustrated and described in connection with FIG. 10 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A system for performing a peritoneal dialysis therapy comprising:
   at least one dialysis fluid pump; and
   a control unit operable with the at least one dialysis fluid pump to perform a plurality of peritoneal dialysis cycles, the cycles including a fill phase, a dwell phase and a drain phase, the control unit configured, upon a user selection to perform a continuous cycling peritoneal dialysis ("CCPD") therapy, to:
   (i) avoid a maximum peritoneal volume being exceeded after any of the dwell phases of the plurality of patient cycles,
   (ii) ensure that a prescribed total sum of dialysis fluid volume of the fill phases is delivered to the patient, and
   (iii) determine if (1) a residual volume left in the patient after one of the drain phases based on a minimum drain percentage will cause the maximum peritoneal volume in (i) to be exceeded during a next cycle, and if the determination in (1) is yes, determine if (2) a threshold minimum drain percentage after the one of the drain phases cannot be achieved,
      if the determination in (2) is yes, activate an alarm, and
      if the determination in (2) is no, reduce an amount of dialysis fluid volume of the fill phase of the next cycle and add an extra cycle to the peritoneal dialysis therapy so that (ii) is satisfied.

2. The system for performing a peritoneal dialysis therapy of claim 1, wherein for the first cycle, satisfying (i) includes ensuring that the prescribed fill volume plus an expected ultrafiltration volume per cycle is less than the maximum peritoneal volume.

3. The system for performing a peritoneal dialysis therapy of claim 1, wherein satisfying (i) includes ensuring that the fill volume plus an expected ultrafiltration volume per cycle plus a residual volume of fluid leftover from a previous drain phase is less than the maximum peritoneal volume.

4. The system for performing a peritoneal dialysis therapy of claim 3, wherein the expected ultrafiltration volume is a percentage of the fluid volume of the fill phase as prescribed.

5. The system for performing a peritoneal dialysis therapy of claim 1, wherein the control unit in (iii) is configured to reduce the amount of the dialysis fluid volume for each of the remaining fill phases.

6. The system for performing a peritoneal dialysis therapy of claim 1, wherein the control unit in (iii) is configured to reduce the amount of the dialysis fluid volume of each of the remaining fill phases by a same amount.

7. The system for performing a peritoneal dialysis therapy of claim 1, wherein the control unit in (iii) is configured to reduce the amount of the dialysis fluid volume for each of the remaining fill phases to an amount equal to a remaining portion of the total sum of dialysis fluid volume divided by a remaining number of cycles including the extra cycle.

8. The system for performing a peritoneal dialysis therapy of claim 7, wherein the control unit is further configured to change the minimum drain percentage to be the reduced fill amount plus an expected ultrafiltration volume per cycle adding to a volume that is divided by the maximum peritoneal volume.

9. The system for performing a peritoneal dialysis therapy of claim 1, wherein the control unit is configured to perform (iii) a plurality of times if needed.

10. The system for performing a peritoneal dialysis therapy of claim 1, wherein the control unit in (iii) is configured to (a) reduce the amount of the dialysis fluid volume of each of the remaining fill phases to a first amount equal to a first remaining portion of the total sum of dialysis fluid volume divided by the remaining number of cycles including the first added cycle, and if needed to (b) reduce the amount of the dialysis fluid volume of each of the remaining fill phases to a second amount equal to a second remaining portion of the total sum of dialysis fluid volume divided by the remaining number of cycles including a second added cycle.

11. The system for performing a peritoneal dialysis therapy of claim 10, wherein the control unit is further configured to (c) change the minimum drain percentage a first time in (a) to the first amount plus an expected ultrafiltration volume adding to a first volume that is divided by the maximum peritoneal volume and (d) change the minimum drain percentage a second time in (b) to the second amount plus an expected ultrafiltration volume adding to a second volume that is divided by the maximum peritoneal volume.

12. The system for performing a peritoneal dialysis therapy of claim 11, wherein the expected ultrafiltration volume in (c) is different than the expected ultrafiltration volume in (d) due to the reduced first amount being different than the reduced second amount.

13. The system for performing a peritoneal dialysis therapy of claim 1, wherein the control unit is further configured to reduce a duration of the dwell phase in the next cycle.

14. The system for performing a peritoneal dialysis therapy of claim 1, wherein the control unit is configured to perform (iii) upon a user election to modify an initially prescribed peritoneal dialysis therapy or (iii) automatically.

15. A system for performing a peritoneal dialysis therapy comprising:
   at least one dialysis fluid pump; and
   a control unit operable with the at least one dialysis fluid pump to perform a plurality of peritoneal dialysis cycles, the cycles including a fill phase, a dwell phase and a drain phase, the control unit configured to:
   (i) ensure that a prescribed total sum of dialysis fluid volume of the fill phases is delivered to the patient, and
   (ii) determine if (1) a minimum drain percentage after one of the drain phases cannot be achieved, and if the determination in (1) is yes, determine if (2) a threshold minimum drain percentage after the one of the drain phases cannot be achieved,
   if the determination in (2) is yes, activate an alarm, and
   if the determination in (2) is no, reduce an amount of dialysis fluid volume of the fill phase of the next cycle and add an additional cycle to the peritoneal dialysis therapy so that (i) is satisfied.

16. The system for performing a peritoneal dialysis therapy of claim 15, wherein the control unit in (ii) is configured to reduce the amount of the dialysis fluid volume for each of the remaining fill phases.

17. The system for performing a peritoneal dialysis therapy of claim 16, wherein the control unit in (ii) is configured to reduce the amount of the dialysis fluid volume for each of the remaining fill phases to an amount equal to a remaining portion of the total sum of dialysis fluid volume divided by a remaining number of cycles including the added cycle.

18. The system for performing a peritoneal dialysis therapy of claim 15, wherein the control unit is further configured to change the minimum drain percentage to the reduced fill amount plus an expected amount of ultrafiltration leading to an outcome that is divided by the maximum peritoneal volume.

19. The system for performing a peritoneal dialysis therapy of claim 15, wherein the control unit is further configured to reduce a duration of the dwell phase in the next cycle.

20. The system for performing a peritoneal dialysis therapy of claim 15, wherein the control unit is further configured to perform (i) and (ii) upon a user election to perform a continuous cycling peritoneal dialysis therapy as opposed to a tidal dialysis therapy.

21. The system for performing a peritoneal dialysis therapy of claim 15, wherein the control unit is configured to perform (ii) upon a user election to modify an initially prescribed peritoneal dialysis therapy or to perform (ii) automatically based on a setting preconfigured by a clinician.

22. A system for performing peritoneal dialysis comprising:
   at least one dialysis fluid pump; and
   a control unit operable with the at least one dialysis fluid pump to perform a plurality of peritoneal dialysis cycles, the cycles including a fill phase, a dwell phase and a drain phase, the control unit configured, upon a user election to perform a continuous cycling peritoneal dialysis ("CCPD") therapy, to:
   (i) ensure that at the end of the dwell phase of each cycle, a maximum peritoneal volume is not exceeded,
   (ii) ensure that a prescribed total sum of dialysis fluid volume over the fill phases of the cycles is delivered to the patient, and
   (iii) monitor each drain phase to ensure (1) a minimum drain volume is met, and if not, determine if (2) a threshold minimum drain volume is met,
   if the determination in (1) and (2) is no, activate an alarm, and
   if the determination in (1) is no and (2) is yes shorten a subsequent fill phase to comply with (i) and add a cycle to comply with (ii).

23. The system for performing peritoneal dialysis of claim 22, which includes a total prescribed time for the cycles in aggregate, the control unit further configured to lessen a duration of at least one subsequent dwell phase if a cycle is added in (iii).

24. The system for performing a peritoneal dialysis therapy of claim 22, wherein the control unit is configured to perform (iii) upon a user election to modify an initially prescribed peritoneal dialysis therapy.

25. The system for performing a peritoneal dialysis therapy of claim 22, wherein the minimum drain volume is the maximum peritoneal volume−(fill phase volume plus an expected ultrafiltrate volume per cycle).

26. A system for performing a peritoneal dialysis therapy comprising:
- at least one dialysis fluid pump; and
- a control unit operable with the at least one dialysis fluid pump to perform a plurality of peritoneal dialysis cycles, the cycles including a fill phase, a dwell phase and a drain phase, the control unit configured to:
  (i) store a previously entered continuous cycling peritoneal dialysis ("CCPD") therapy having a total prescribed fresh dialysate fill volume delivered over n cycles, the cycles performed over a total therapy duration; and
  (ii) automatically convert the CCPD therapy into a tidal peritoneal dialysis therapy having n+1 cycles, using the total prescribed fresh dialysis fill volume, and maintaining the total therapy duration,
- wherein the control unit is configured to provide an option to perform (ii), wherein the tidal therapy is a first tidal therapy or to instead perform (iii), wherein the CCPD therapy is automatically converted to a second tidal therapy having n+2 cycles, using the prescribed total fresh dialysate fill volume, and maintaining the total therapy duration.

27. The system for performing a peritoneal dialysis therapy of claim 26,
wherein the control unit is configured to shorten individual drain times for at least some of the drain phases for at least one of (ii) and (iii) such that a specified amount of residual volume is left within a patient for the at least some of the drain phases.

28. The system for performing a peritoneal dialysis therapy of claim 26, wherein the first tidal therapy has a prescribed first residual drain volume and the second tidal therapy has a prescribed second, higher, residual drain volume.

29. The system for performing a peritoneal dialysis therapy of claim 26, wherein the control unit is further configured to perform (i) and (ii) upon a user's election to perform a tidal therapy peritoneal dialysis as opposed to a CCPD dialysis therapy.

30. The system for performing a peritoneal dialysis therapy of claim 26, wherein the control unit is further configured such that a volume residing in a patient after each of the fills of the tidal therapy is at least substantially equal to the volume that would reside in the patient after each of the fills of the CCPD therapy.

31. The system for performing a peritoneal dialysis therapy of claim 1, wherein the minimum drain percentage is greater than the threshold minimum drain percentage.

* * * * *